(12) United States Patent
Tse et al.

US010252260B2

(10) Patent No.: US 10,252,260 B2
(45) Date of Patent: Apr. 9, 2019

(54) SYSTEM AND METHOD FOR DEFORMING PARTICLES

(71) Applicant: CytoVale Inc., South San Francisco, CA (US)

(72) Inventors: Henry Tse, South San Francisco, CA (US); Kate Crawford, South San Francisco, CA (US); Ajay Shah, South San Francisco, CA (US)

(73) Assignee: CytoVale Inc., San Francisco, CA (US)

( * ) Notice: Subject to any disclaimer, the term of this patent is extended or adjusted under 35 U.S.C. 154(b) by 0 days.

(21) Appl. No.: 15/477,973

(22) Filed: Apr. 3, 2017

(65) Prior Publication Data

US 2017/0284924 A1 Oct. 5, 2017

Related U.S. Application Data

(60) Provisional application No. 62/316,742, filed on Apr. 1, 2016.

(51) Int. Cl.
*G01N 15/14* (2006.01)
*B01L 3/00* (2006.01)
*G01N 15/10* (2006.01)

(52) U.S. Cl.
CPC ............ *B01L 3/00* (2013.01); *G01N 15/1459* (2013.01); *G01N 15/1463* (2013.01); *G01N 2015/1006* (2013.01); *G01N 2015/1495* (2013.01)

(58) Field of Classification Search
CPC .............................................. G01N 2015/1006
See application file for complete search history.

(56) References Cited

U.S. PATENT DOCUMENTS

| 5,798,827 | A | 8/1998 | Frank et al. |
| 8,935,098 | B2 | 1/2015 | Di Carlo et al. |
| 9,151,705 | B2 | 10/2015 | Di Carlo et al. |
| 9,464,977 | B2 | 10/2016 | Di Carlo et al. |
| 2006/0139638 | A1 | 6/2006 | Muller et al. |
| 2016/0231224 | A1 | 8/2016 | Di Carlo et al. |

FOREIGN PATENT DOCUMENTS

| JP | 2001-211896 | 8/2001 |
| JP | 2009-511998 | 3/2009 |
| KR | 100889617 | 3/2009 |
| KR | 100889618 | 3/2009 |
| KR | 100965222 | 6/2010 |
| WO | 113908 | 12/2004 |
| WO | 047761 | 4/2007 |
| WO | 069418 | 6/2009 |
| WO | 040067 | 3/2012 |

OTHER PUBLICATIONS

Bhagat, Ali Asgar; et al., Intertial microfluidics for sheath-less high-throughput cytometry, Biomed. Microdevices 12(2), 187-195 (2010).
Bow, Hansen; et al., A microfabricated deformability-based flow cytometer with application to malaria, Lab Chip. Mar. 21, 2011; 11(6): 1065-1073. doi:10.1039/c0lc00472c.
Cha, Sukgyen; et al., Cell Stretching Measurement Utilizing Viscoelastic Particle Focusing, Anal. Chem., 2012, 84, 10471-10477.
Chambers, Ann F.; et al., Metastasis: dissemination and growth of cancer cells in metastatic site, Nature Reviews cancer, vol. 2(8), p. 563-572, 2002.
Chen, J.; et al., Classification of cell types using a microfluidic device for mechanical and electrical measurement on single cells, Lab Chip, 2011, 11, 3174-3181.
Choi, Sungyoung; et al., Sheathless hydrophoretic particle focusing in a microchannel with exponentially increasing obstacle arrays, Anal Chem., 80(8):3035-9 (2008).
Cross, Sarah E.; et al., Nanomechanical analysis of cells from cancer patients. Nat Nano 2:780-783 (2007).
Di Carlo, Dino, Inertial microfluidics. Lab Chip 9:3038-3046 (2009).
Di Carlo, Dino; et al., Continuous inertial focusing, ordering, and separation of particles in microchannels. Proc Natl Acad Sci USA 104:18892-18897 (2007).
Di Carlo, Dino; et al., Dynamic Single-Cell Analysis for Quantitative Biology, Analytical Chemistry 78:7918-7925 (2006).
Di Carlo, Dino; et al., Particle Segregation and Dynamics in Confined Flows, Phys. Rev. Lett. 102 (2009).
Dobbe, J.G.G.; et al., Measurement of the Distribution of Red Blood Cell Deformability Using an Automated Rheoscope, Cytometry (Clinical Cytometry), vol. 50, pp. 313-325, 2002.
Dudani, Jaideep S.; et al., Pinched-flow hydrodynamic stretching of single-cells+, Lab Chip, 2013, 13, 3728.
Dylla-Spears, Rebecca; et al., Single-molecule detection via microfluidic planar extensional flow at a stagnation point, Lab on a Chip, vol. 10, pp. 1543-1549, Mar. 2010.
Gossett, "Deformability Cytometry: High-Throughput, Continuous Measurement of Cell Mechanical Properties in Extensional Flow", 14th International Conference on Miniaturized System of Chemistry and Life Sciences Oct. 3-7, 2010, Groningten, The Netherlands (pp. 1382-1384).

(Continued)

*Primary Examiner* — Bin Shen
(74) *Attorney, Agent, or Firm* — Jeffrey Schox

(57) ABSTRACT

Embodiments of a system and method for deforming a can include a substrate including an inlet module and an outlet module; a fluidic pathway coupled to the inlet module and the outlet module, and including a sample branch operable to transmit the sample fluid; one or more sheath fluid branches flanking the sample branch and operable to transmit sheath having a sheath fluid viscosity higher than a sample fluid viscosity of the sample fluid; a delivery region initiating at a junction between the sample branch and the one or more sheath fluid branches, and operable to transmit a co-flow comprising the sample fluid and the sheath fluid; and a deformation region located downstream of the delivery region and operable to deform the one or more particles of the sample fluid based upon a reduced velocity of the sheath fluid with respect to the sample fluid in the co-flow.

10 Claims, 16 Drawing Sheets

(56) References Cited

OTHER PUBLICATIONS

Gossett, Daniel R.; et al., Hydrodynamic stretching of single cells for large population mechanical phenotyping, 7630-7635, PNAS, May 15, 2012, vol. 1091, No. 20.
Gossett, Daniel R.; et al., Leukocyte Mechanophenotyping by Deformability Cytometry, 16th International Conference on Miniaturized Systems for Chemistry and Life Sciences Oct. 28-Nov. 1, 2012, Okinawa, Japan (3pages).
Gossett, Daniel R.; et al., Particle focusing mechanisms in curving confined flows, Anal Chem 81:8459-8465 (2009).
Guck, J.; et al., Optical Deformability as an Inherent Cell Marker for Testing Malignant Transformation and Metastatic Competence, Biophysical Journal, vol. 88, May 2005, 3689-3698.
Guo, Q., Microfluidic Device for Measuring the Deformability of Single Cells, Doctorate Thesis, The University of British Columbia, Apr. 2012, 1-24 (total 78 pages.
Lee, Wonhee; et al., Dynamic self-assembly and control of microfluidic particle crystals, Proc. Natl. Acad. Sci. U.S.A 107, 22413-22418 (2010).
Lincoln, Bryan; et al., Deformability-Based Flow Cytometry, Cytometry Part A, vol. 59A, pp. 203-209, 2004.
Mao, Xiaole; et al., single-layer planar on-chip flow cytometer using microfluidic drifting based three-dimensional (3D) hydrodynamic focusing, Lab Chip, 9, 1583-1589 (2009).
Oakey, John; et al., Particle Focusing in Staged Inertial Microfluidic Devices for Flow Cytometry, Anal. Chem., 82, 3862-3867 (2010).
Park, Jae-Sung; et al., Continuous focusing of microparticles using intertial lift force and vorticity via multi-orifice microfluidic channels, Lab on a Chip, 9, 939-48 (2009).
Perkins, Thomas T.; et al., Single Polymer Dynamics in an Elongational Flow, Science 276:2016-2021 (1997).
Shelby, Patrick J.; et al., A microfluidic model for single-cell capillary obstruction by Plasmodium falciparum-infected erythrocytes, PNAS, vol. 100, pp. 14618-14622, 2003.
Squires, Todd M.;, Microfluidics: Fluid physics at the nanoliter scale, Rev. of Modem Physics, vol. 77, pp. 977-1026, 2005.
Sraj, Ihab; et al., Cell deformation cytometry using diode-bar optical stretchers, J Biomed Opt 15 (2010).
Suresh, S.; et al., Connections between single-cell biomechanics and human disease states: gastrointestinal cancer and malaria. Acta Biomater 1:15-30 (2005).
Thery, Manuel; et al., Get round and stiff for mitosis. HFSP J 2:65-71 (2008).
Yamada, Masumi; et al., Hydrodynamic filtration for on-chip particle concentration and classification utilizing microfluidics Lab Chip, 5, 1233-1239 (2005).
Yap, Belinda; et al., Cystoskeletal remodeling and cellular activation during deformation of neutrophils into narrow channels, J. Appl. Physiol, vol. 99, pp. 2323-2330, 2005.
Young, Susan M.; et al., High-Throughput Microfluidic Mixing and Multiparametric Cell Sorting for Bioactive Compound Screening, J. Biomol Scree, vol. 9, pp. 103-111, 2004.
Zheng, Bo; et al., Formation of Droplets of Alternating Composition in Microfluidic Channels and Applications to Indexing of Concentrations in Droplet-Based Assays, Anal. Chem., vol. 76, pp. 4977-4982, 2004.

VELOCITY PROFILES

SYSTEM AND METHOD FOR DEFORMING PARTICLES

CROSS-REFERENCE TO RELATED APPLICATIONS

This application claims the benefit of U.S. Provisional Application Ser. No. 62/316,742, filed on 1 Apr. 2016, which is incorporated herein in its entirety by this reference.

TECHNICAL FIELD

This invention relates generally to the microfluidics field, and more specifically to an improved system and method for deforming and analyzing particles such as cells in the microfluidics field.

BACKGROUND

There is growing evidence that cell deformability is a useful indicator of abnormal cytoskeletal changes, and can provide a label-free biomarker for determining cell states or properties, such as metastatic potential, cell cycle stage, degree of differentiation, and leukocyte activation. Clinically, a measure of metastatic potential and/or other factors could guide treatment decisions, or a measure of degree of differentiation could prevent transplantation of undifferentiated tumorigenic stem cells in regenerative therapies. For drug discovery and personalized medicine, a measure of cytoskeletal integrity could allow screening for cytoskeletal-acting drugs or evaluation of cytoskeletal drug resistance in biopsied samples. Cell deformability can further provide insight into mechanotransduction pathways for different cell lines, opening new avenues of discovery in cellular biomechanics. Currently, implementation of these techniques and analyses is cost-prohibitive and labor-intensive, which is a substantial limiting factor in clinical and research applications. Current platforms for cell deformation techniques and analyses suffer from a large number of limitations, including one or more of the following: limited throughput, inconsistency, limited characterization of sample heterogeneity, speed, and labor intensity. In particular, platforms optimized for biophysics research operate at rates of approximately 1 cell/minute, which significantly hampers one's ability to process and analyze a large number of heterogeneous particles. Thus, there is a need in the cytometer field to create a new and improved system and method for deforming and analyzing particles. This invention provides such a new and improved system and method.

DESCRIPTION OF THE PREFERRED EMBODIMENTS

The following description of preferred embodiments and examples of the invention is not intended to limit the invention to these preferred embodiments and examples, but rather to enable any person skilled in the art to make and use this invention.

1. Overview.

Figure 3:
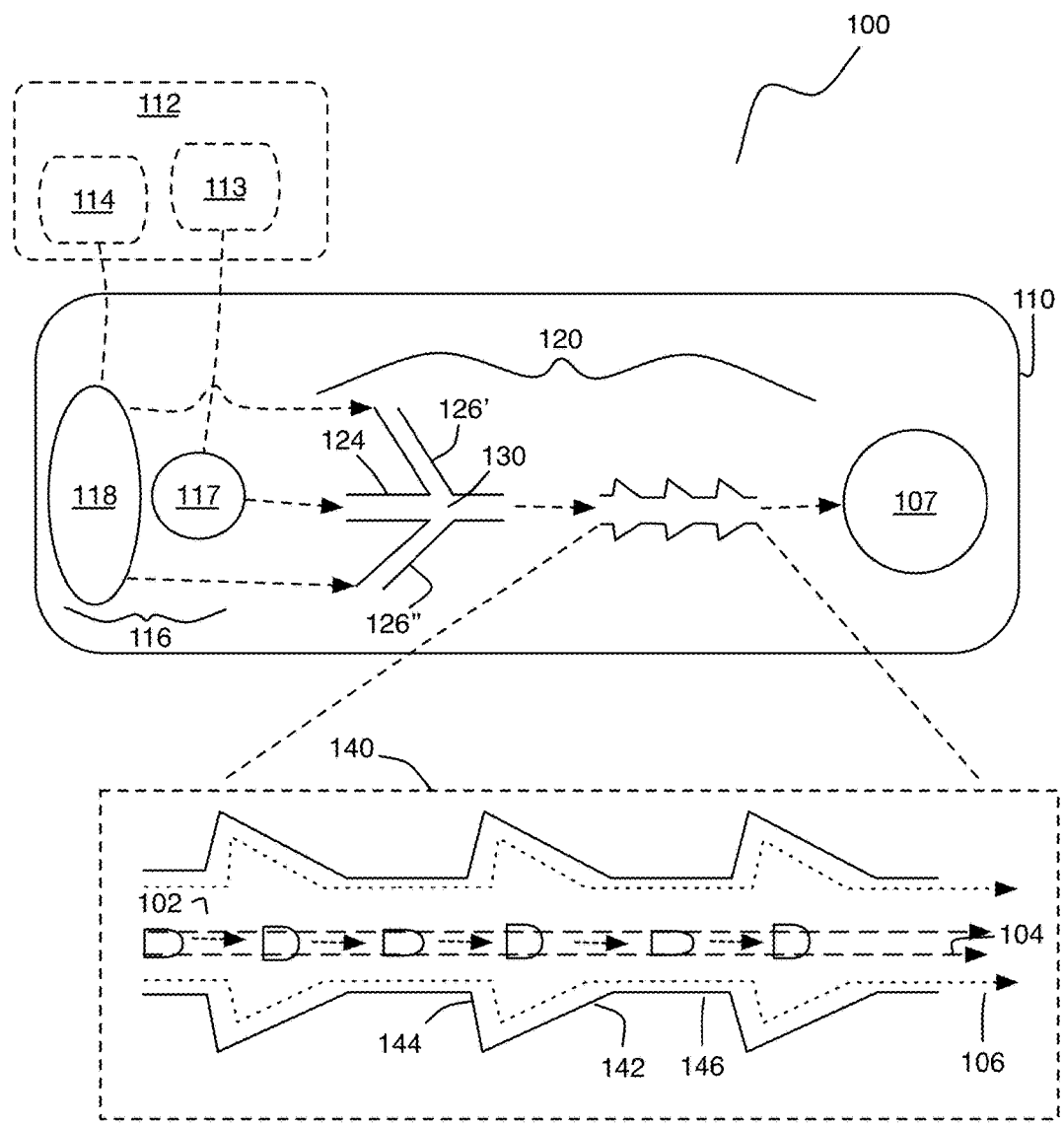
FIG. 3 is a schematic representation of an embodiment of a system for deforming particles.

As shown in FIG. 3, embodiments of a system 10o for deforming one or more particles of a sample fluid can include a substrate including an inlet module and an outlet module; a fluidic pathway coupled to the inlet module and the outlet module, and including a sample branch coupled to a sample inlet and operable to transmit the sample fluid; one or more sheath fluid branches (e.g., a pair of sheath fluid branches) flanking the sample branch and coupled to a sheath inlet; the sheath fluid branches operable to transmit a sheath fluid having a sheath fluid viscosity higher than a sample fluid viscosity of the sample fluid (e.g., or a sheath fluid viscosity lower than the sample fluid viscosity); a delivery region initiating at a junction between the sample branch and the one or more sheath fluid branches, and operable to receive the sample fluid and the sheath fluid, and operable to transmit a co-flow including the sample fluid and the sheath fluid; a deformation region located downstream of the delivery region and operable to deform the one or more particles of the sample fluid based upon a reduced velocity of the sheath fluid (e.g., or a higher velocity of the sheath fluid, such as when the sheath fluid viscosity is lower than the sample fluid viscosity) with respect to the sample fluid in the co-flow (e.g., laminar co-flow), where in some embodiments the deformation region includes one or more narrowing regions, expanding regions, and/or straight regions.

Further, in some variations, the system 100 can additionally alternatively include a detection module, a processor, a storage module, a filter, a processed sample volume receiver, and/or other suitable components analogous to embodiments, variations, and examples described in U.S. application Ser. No. 14/057,942, entitled "SYSTEM AND METHOD FOR DEFORMING AND ANALYZING PAR- TICLES" and filed on 18 Oct. 2013, which is incorporated herein in its entirety by this reference.

Figure 10:
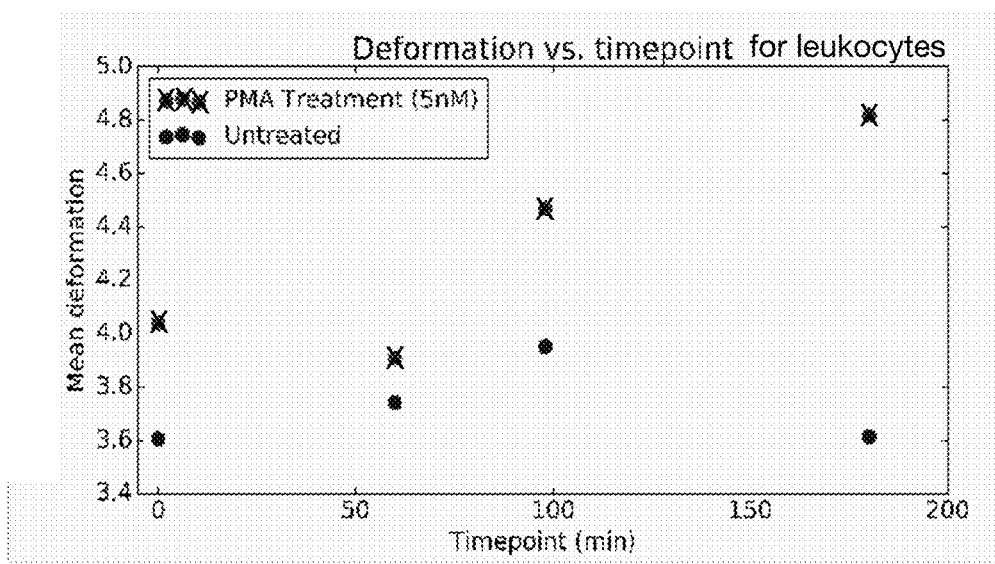
FIG. 10 illustrates the bullet metric as a function of treatment time for white blood cells treated with 5 nM phorbol 12-myristate as compared with a untreated control in embodiments of a system and method for deforming particles.
Figure 11A:
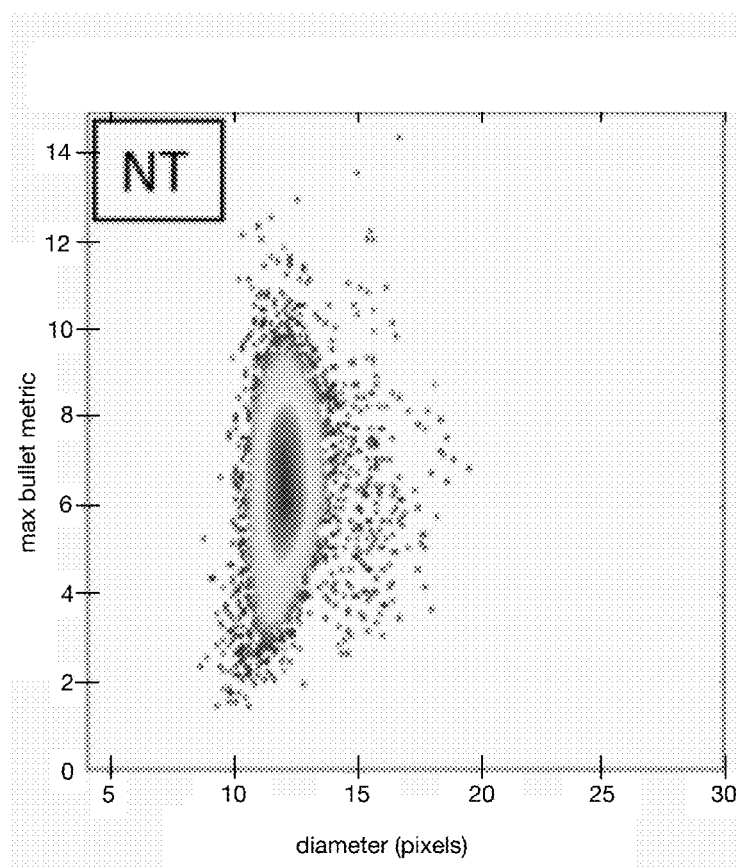
FIGS. 11A-11C illustrate bullet metric as a function of size for red blood cells treated with different concentrations of primaquine in variations of a system and method for deforming particles.
Figure 11B:
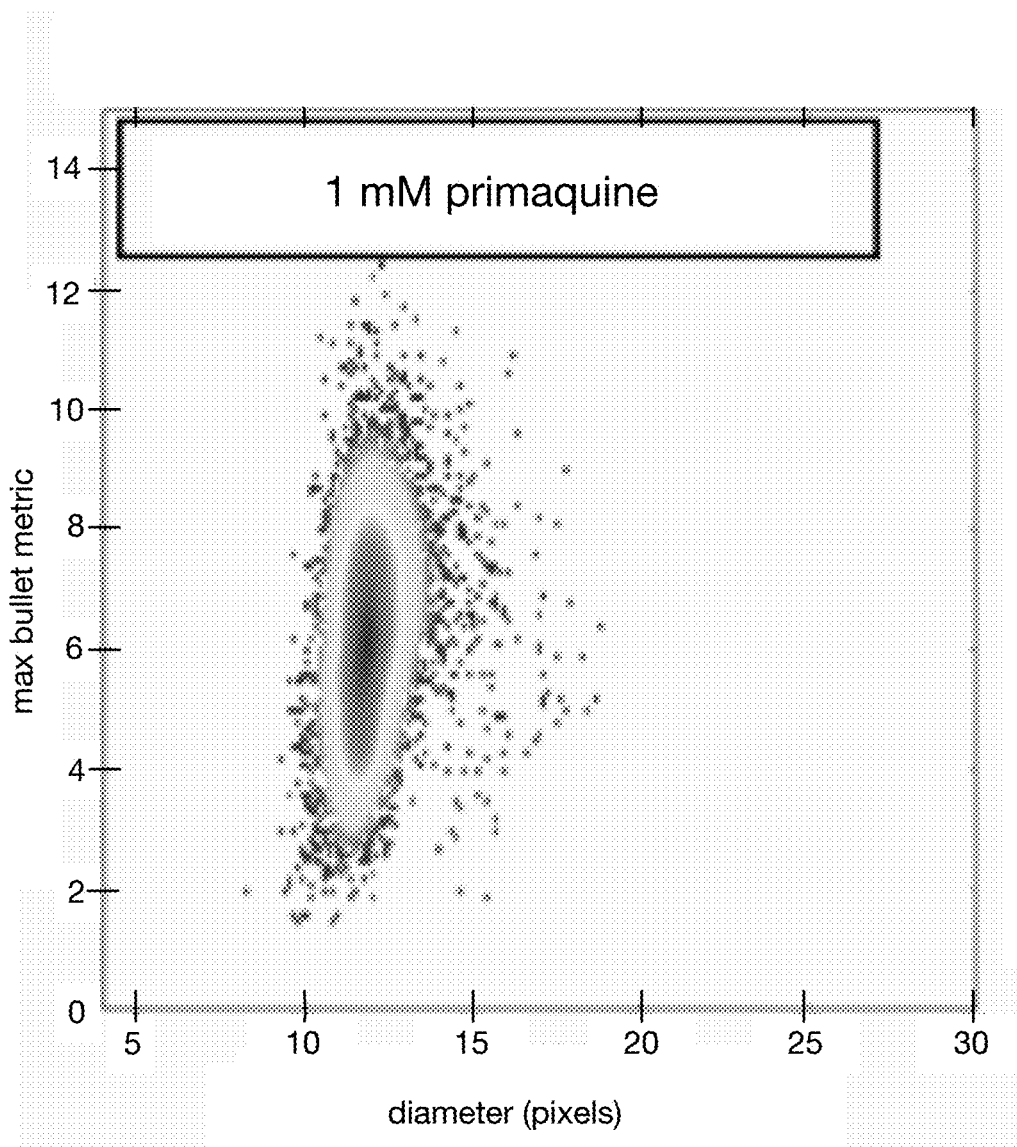
Figure 11C:
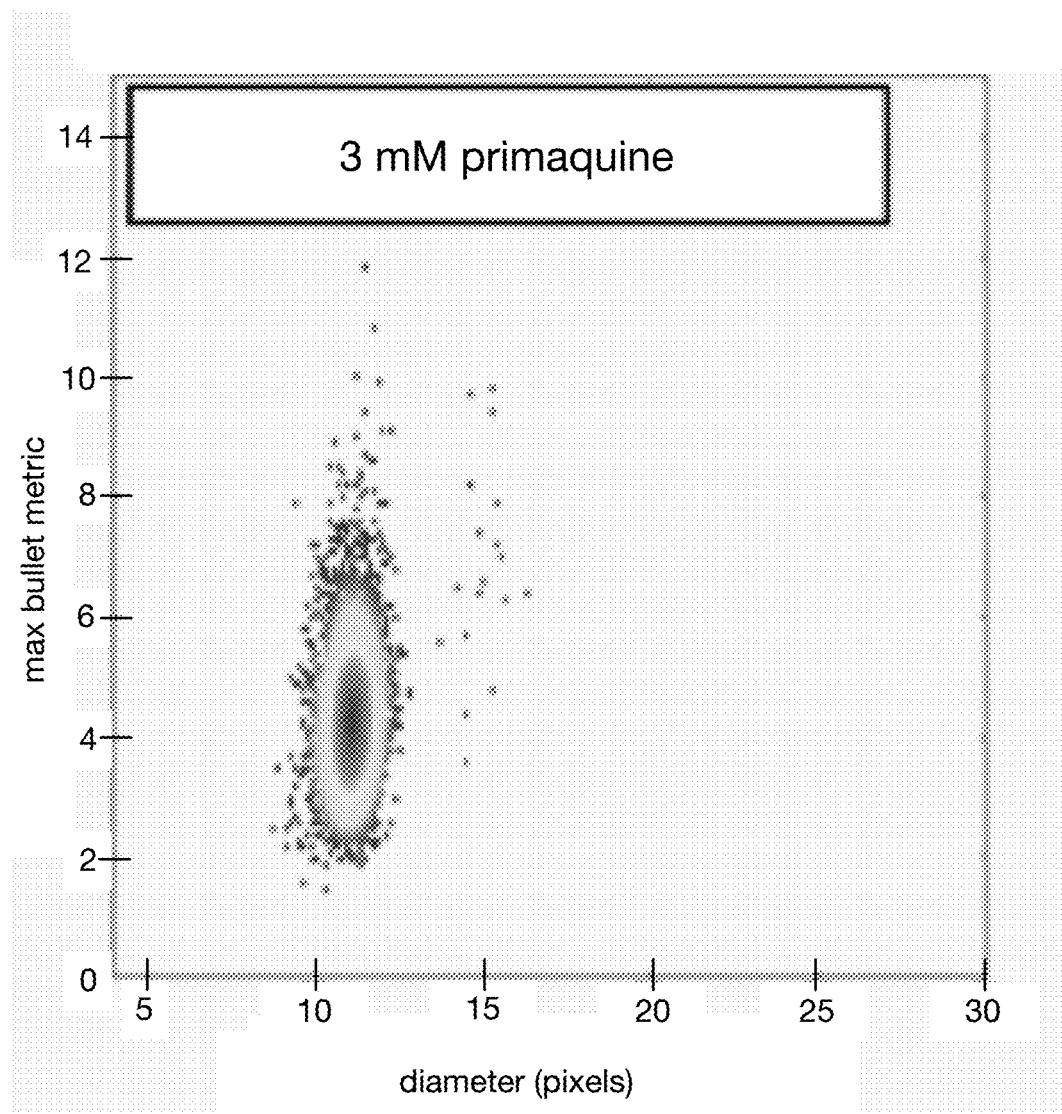

The system 100 and/or method 200 function to enable the deformation of individual particles in a high-throughput and consistent manner, with the ability to simultaneously generate and analyze multiple data types characterizing the single particles. In one embodiment, the system 100 and/or method 200 further function to enable the generation of data that directly correlates mechanical properties of the particles with one or more fluorescence characterizations of the particles (e.g., fluorescent antibody stains, live/dead cell stains, nuclear stains, stains for apoptosis, fluorescent proteins, etc.) at the single-particle level. This can allow the generation of a direct quantitative comparison between biomolecular properties and mechanical properties. Preferably, the system 100 and/or method 200 is used to process and analyze biological particles, such as cells, and in a specific application, the system 100 and/or method 200 can be used to diagnose and/or characterize a sepsis-related condition, or characterize immune cell activation status in a patient providing the biological sample containing cells, based on mechanical parameters of the cells (e.g. leukocytes) undergoing deformation. Additionally or alternatively, in other specific applications, the system 100 and/or method 200 can be used to characterize one or more of: leukocyte activation, stem cell differentiation, cellular response to drugs, and cancer cell malignancy by way of correlating cellular deformation with cell state or biomolecular phenotypes. In an example, biomodels for characterizing correlations between mechanical properties and different cell states can be developed with the system 100 and/or method 200 using fluids with different viscosities. In specific examples, a primaquine biphosphate biomodel can be developed for measuring mechanical properties for particles with different stiffness, where FIGS. 11A-11C illustrate diameter (in pixels, where 1 pixel can equal ⅔ μm and/or other suitable distances) versus bullet metric for red blood cells of different stiffness induced by different concentrations of primaquine, and where a decrease in a cell morphological metric (e.g. bullet metric) is observed with increasing concentrations of primaquine. In another specific example, white blood cells treated with 5 nM of phorbol 12-myristate show an increased change in a cell morphological metric over treatment time as compared to untreated controls, as illustrated in FIG. 10. Besides correlating to biomolecular phenotypes, combining biomolecular and deformability-based data can provide additional classification accuracy. However, the system 100 and/or method 200 can alternatively be used to process, deform, and analyze any other suitable biological particle or non-biological particles.

Figure 12A:
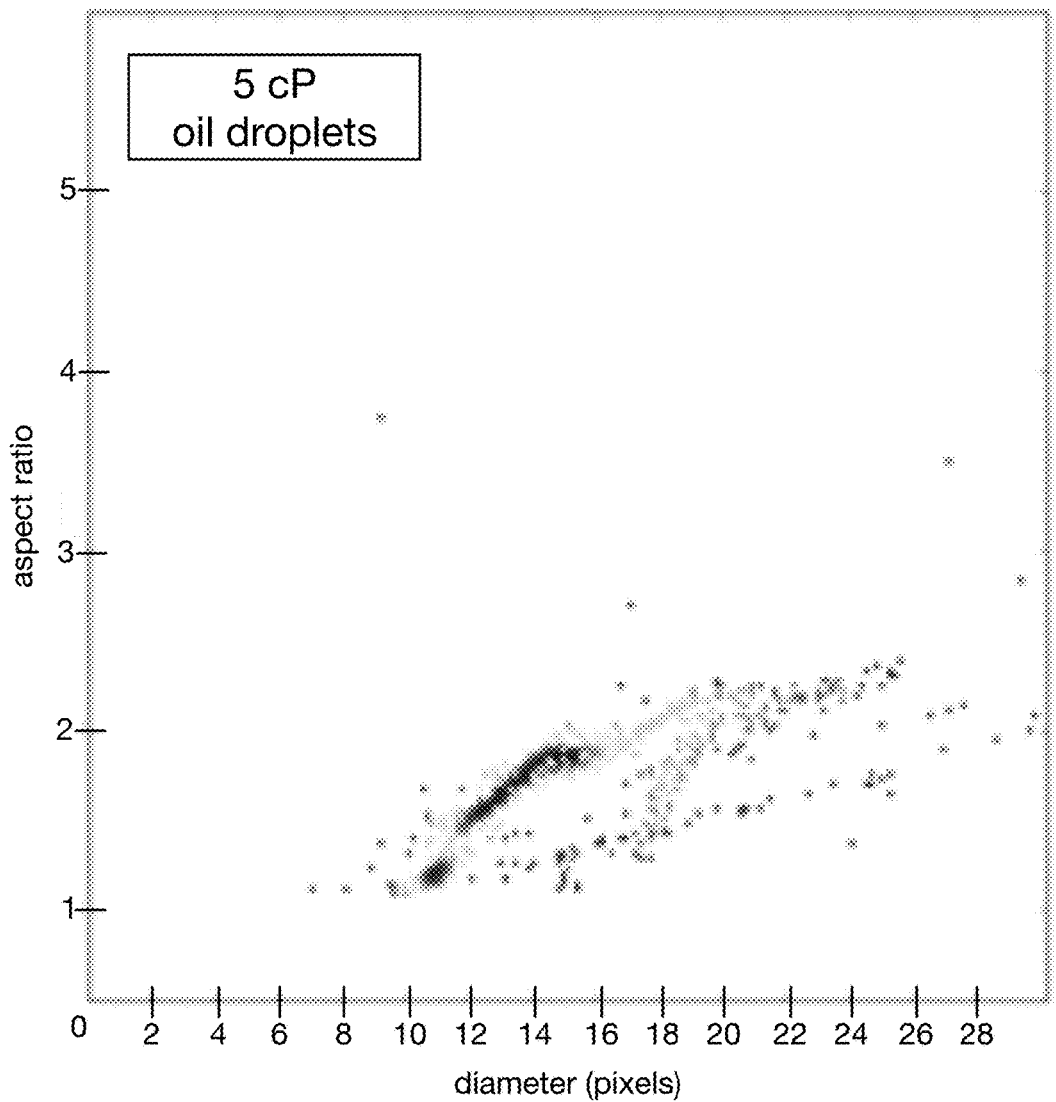
FIGS. 12A-12C illustrate aspect ratio as a function of oil droplet size in variations of a system and method for deforming particles.
Figure 12B:
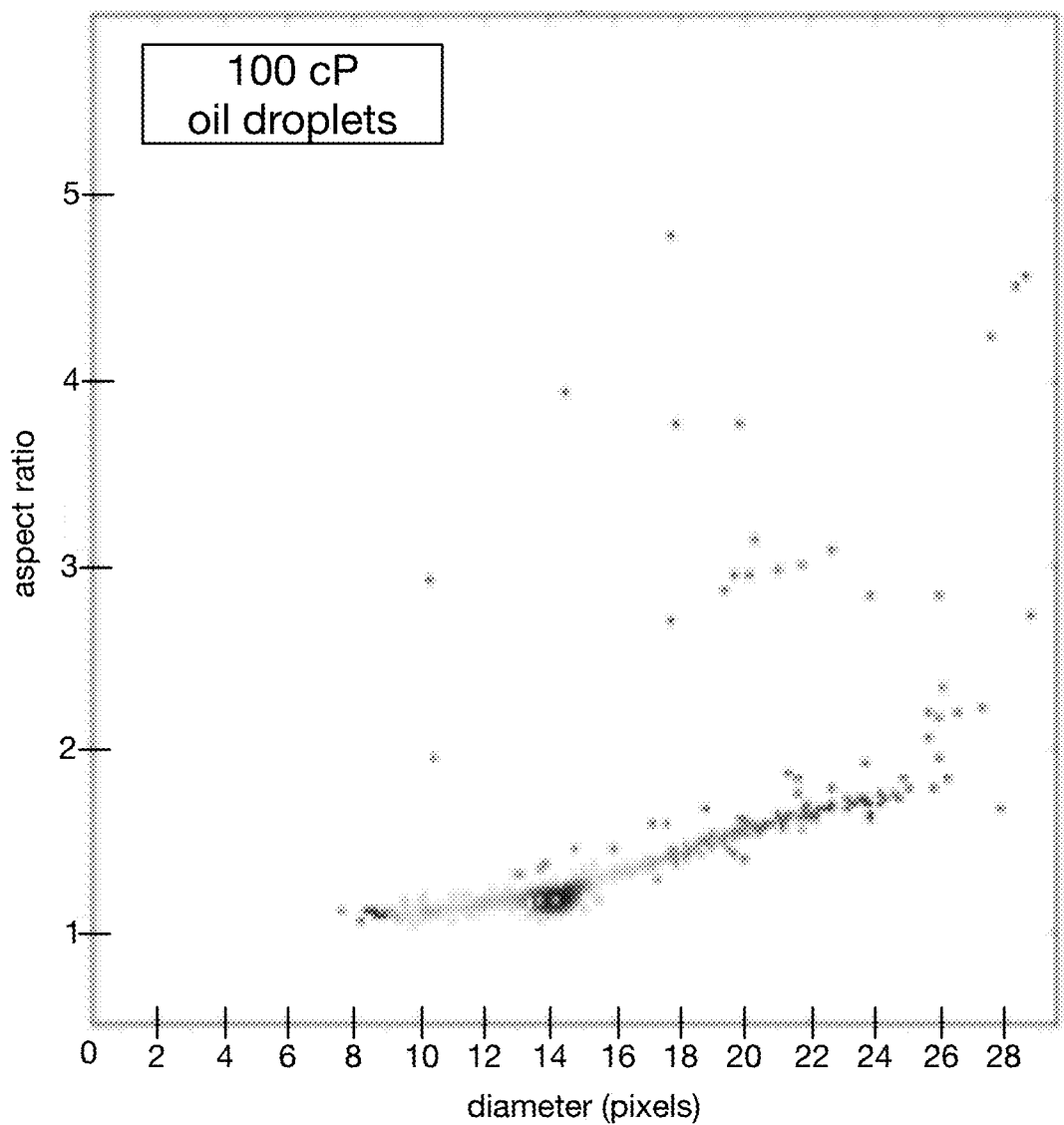
Figure 12C:
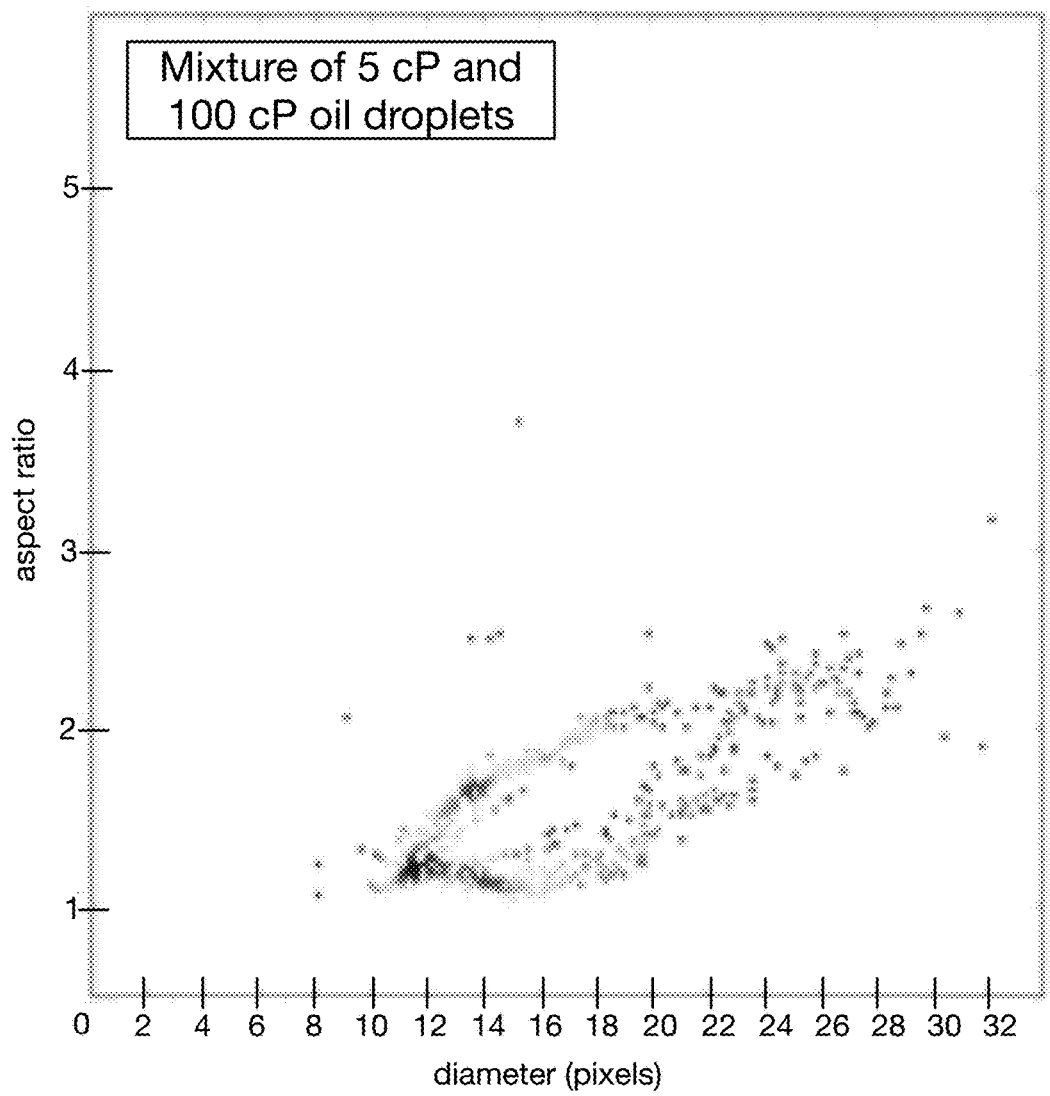

Preferably, a particle is a small object that can be contained within fluid flow (e.g., >1 μm in diameter). The specific particle populations in the sample can be any one or more of: cells (e.g., specific leukocyte subpopulations, immune cells, circulating tumor cells, circulating endothelial cells, circulating endothelial progenitor cells, circulating stem cells, non-circulating cells, etc.), and populations of any other suitable particle type. Non-biological particles can include: hydrogel particles, droplets, bubbles, vesicles or other polymer-based particles. Non-biological particles can be used in the system alone to measure the distribution of their mechanical properties, or if properties are well controlled can be mixed with biological particles, where such mechanical properties can facilitate calibration of the deformation characteristics of the biological particles and normalization between experiments. In examples, deformation metrics for oil droplets of different viscosities can be measured with the system 100 and/or method 200, where diameter versus aspect ratio can be seen in FIGS. 12A-12C for oil droplets of 5 cP, 100 cP, and a mixture of 5 cP and 100 cP oil droplets.

Figure 4:
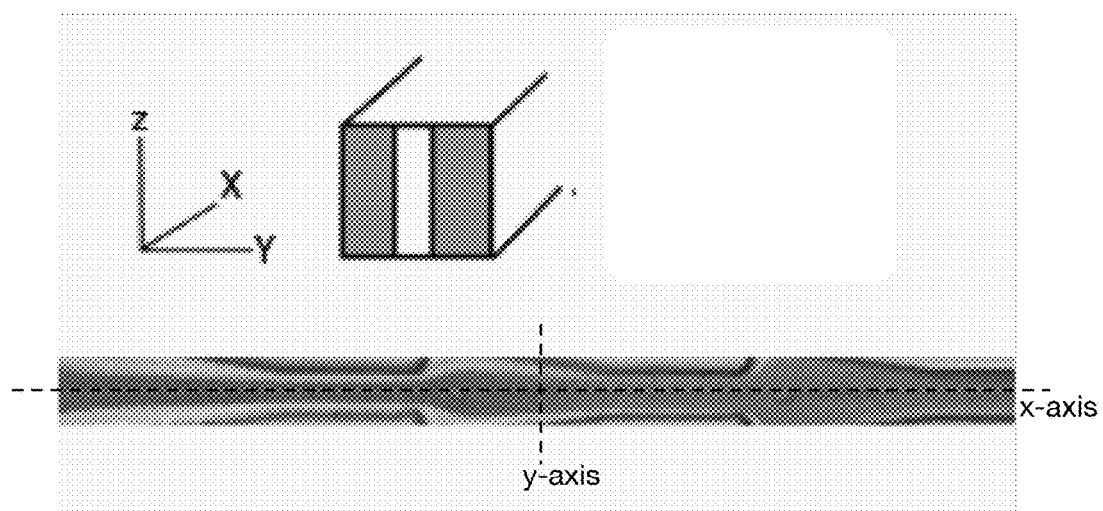
FIG. 4 is a schematic representation of axes associated with a fluidic pathway in embodiments of a system and method for deforming particles.

The system 100 and method 200 are preferably associated with axes (e.g., where the x-axis is preferably substantially co-axial with the flow axis for a particle traveling through the fluidic pathway) defined in FIG. 4, but can be associated with any suitable axes. However, the system 100 and method 200 can be configured in any suitable manner for facilitating the deformation, assaying, and/or analysis of particles of interest.

2. Benefits

The system and/or method can confer several benefits over conventional methodologies. In specific examples, the system and/or method can confer one or more of the following:

First, the technology can enable a greater velocity gradient and an associated greater viscous stress applied to particles of interest traveling through a deformation region of the system, thereby aiding in the determination of native visco-elastic properties of the particle of interest. In examples, when comparing a viscous co-flow (e.g., a co-flow with a greater viscosity sheath fluid pinching a lesser viscosity sample fluid) to a co-flow of fluids of same or similar viscosity, the viscous co-flow can achieve over a 1.5× greater velocity gradient across a cell (e.g., leukocyte) body. Additionally, in examples, the resulting viscous stress can be at least over an order of magnitude larger than the viscous stress produced in a co-flow of fluids of same or similar viscosity.

Second, the technology can enable repeated cycles of stress (e.g., leading to strain and deformation of the particle) and relaxation through expanding regions, narrowing regions, and/or straight regions of the deformation region. Accordingly, the technology can measure the dynamic phase response of particles of interest and fit the resulting measurements to mechanical model systems to diagnose and/or otherwise characterize human conditions.

Third, the technology can account for different particle types, sizes, and/or other characteristics by tuning co-flow parameters (e.g., sheath fluid parameters, sample fluid parameters) in order to achieve desired velocity profiles and/or viscous stress profiles for illuminating morphological properties of particles of interest.

The technology can, however, provide any benefits described herein, and/or any other suitable benefits in the context of applying the system and method for deforming and/or characterizing particles.

3.1 System—Substrate

The substrate 110 functions to provide a platform by which particles of interest 102 can be deformed and analyzed. Embodiments, variations, and examples of the substrate no are described in U.S. application Ser. No. 14/057,942, entitled "SYSTEM AND METHOD FOR DEFORMING AND ANALYZING PARTICLES" and filed on 18 Oct. 2013, which is incorporated herein in its entirety by this reference.

3.1.A System—Substrate: Inlet Module/Outlet Module

In an embodiment, the microfluidic elements of the substrate no include an inlet module 116 and an outlet module 107 for receiving and transmitting a sample fluid 104 (e.g., with a sample fluid inlet 117) and/or sheath fluid 106 (e.g., with a sheath fluid inlet 118) from the substrate no. The inlet module 116 functions to receive one or more fluid volumes, to initiate processing and analysis of the particles 102 within the substrate no. Preferably, the inlet module 116 is operable to receive fluid volumes from a fluid delivery module including a pump 112; however, the inlet can be operable to receive the sample volume in any other suitable manner. In other variations, the pump 112 can be a syringe pump containing the fluid volume, or any other fluid pump operable to provide at least one of a positive pressure and a negative pressure, in order to deliver the fluid volume into the inlet module 116. Additionally, the pump 112 can be manually or automatically operated, but is preferably operable to transmit the fluid volume into the inlet module 116 at a uniform flow rate (e.g. that can be adjusted between sample runs). Furthermore, the pump 112 can be coupled to any suitable conduit (e.g., tubing, conduit, manifold) operable to transmit the fluid volume (e.g., from a sample well coupled to the substrate no) into the inlet module 116, and can include a valve and/or a pressure sensor in order to control and detect flow parameters. In one specific example, the pump 112 is automatically controlled and operable to provide a flow rate that enables particle focusing (e.g., where the system can include an optical system operable to capture images at a frames per second rate suitable for a flow rate corresponding to the particle focusing, etc.) and achieves a desired particle deformation. Alternatively, the pump 112 can be controlled to achieve a particular particle throughput. Furthermore, in still other alternative examples, the pump 112 can be operable to deliver a fluid volume including particles of interest 102 with a density between 200,000 particles/mL and 8 million particles/mL. As shown in FIG. 3, the fluid delivery module can include multiple pumps 112, such as a sample fluid pump 113 for transmitting sample fluid 104 to a sample fluid inlet 117, and a sheath fluid pump 114 for transmitting sheath fluid 106 to a sheath fluid inlet 118. However, the inlet module 116 and associated pumps 112 can be configured in any suitable manner.

The outlet module 107 functions to transmit the sample volume including the plurality of particles of interest 102 from the substrate 110, after the sample volume has been processed. Preferably, the outlet module 107 is operable to transmit the processed sample volume as waste from the substrate 110; however, the outlet module 107 can alternatively be operable to transmit the processed sample volume from the substrate 110 for further processing and analysis. In one variation, the outlet module 107 can be operable to couple to a waste chamber that is operable to receive waste fluids from the outlet module 107. In this variation, the waste chamber can be integrated (e.g., of unitary construction, physically coextensive) with the substrate 110, such that the outlet module 107 is operable to deliver waste fluids into the waste chamber of the substrate 110. In another variation, the outlet module 107 can be operable to couple to a fluid conduit that delivers the processed sample volume to another module for further processing. Similar to the inlet module 116, the outlet module 107 is preferably operable to form a hermetic seal about a point of coupling (e.g., to a waste chamber, to a module for further processing), and can include any one or more of: a male-female threaded coupling, an o-ring, septum, and a sealant that facilitates generation of the hermetic seal. In other variations, however, the outlet 106 can be operable to couple to any other suitable element in any other suitable manner, for example, using one or more microfluidic conduits or channels.

In a first variation, as shown in FIG. 3, the substrate 110 includes an inlet module 116 with multiple inlets. In an example of the first specific variation, the inlet module 116 includes a sample fluid inlet 117 and a sheath fluid inlet 118. Further, the substrate 110 can also include an outlet of the outlet module 107, the outlet defined at an opposite end of the substrate no. Preferably, the sample fluid inlet 117 is operable to receive the sample fluid 104 containing the one or more particles of interest 102, and the sheath fluid inlet 118 is operable to receive a sheath fluid 106 (e.g., Dextran, methylcellulose, polysorbate, alginate, agarose, polyethylene glycol, phosphate-buffered saline, etc.) with a preferably higher viscosity than the sample fluid 104 (e.g., or the opposite case, with the sample fluid having a higher viscosity than the sheath fluid). Preferably, the sheath fluid has a similar index of refraction with the sample fluid in order to avoid refraction at the interface between the fluids which can prevent accurate imaging of the deforming particle morphology (e.g. an index of refraction less than 20% different and preferably less than 10% or 5% different). In examples, the sheath fluid 106 and/or sample fluid 104 can include 3%-10% Dextran with viscosities from 1-75 cP, but the sheath fluid 106 and/or sample fluid 104 can be associated with any suitable concentrations and viscosities. In a specific example, the sheath fluid 106 can include 3.5% Dextran with viscosity of 15 cP (e.g., for a sample including leukocytes, etc.). In another example, the sheath fluid viscosity can be 5 to 25 fold higher than the sample fluid viscosity. In a preferred embodiment the sample fluid viscosity is similar to water (~1 centipoise). In a specific example, the sample fluid 104 can include 7% Dextran (e.g., for a sample including red blood cells, etc.). In a specific example of a red blood cell application, the sample fluid 104 can include Dextran, and the sheath fluid 106 can include phosphate-buffered saline; further, the sheath fluid composition and sample fluid composition can be switched or otherwise varied based on application and/or particle type (e.g., phosphate-buffered saline for sample fluid 104 and Dextran for sheath fluid 106 for leukocyte applications). The sample fluid 104 can include body fluid directly, or processed body fluid in which, for example, overly abundant red blood cells are lysed or otherwise removed. The sample fluid inlet 117 is further preferably operable to transmit the sample fluid 104 to the sample fluid branch 124 of the fluidic pathway 120, and the sheath fluid inlet 118 is further preferably operable to transmit the sheath fluid 106 to the one or more sheath fluid branches 126, of the fluidic pathway 120. However, the sample fluid inlet 117 and/or sheath fluid inlet 118 can be operable to transmit the sample fluid 104 and/or sheath fluid 106 to any suitable region of the system 100. Preferably, the fluidic resistances of the multiple inlets can be adjusted. In an illustration, the sample fluid inlet 117 and the sheath fluid inlet 118 can be adjusted to have matching fluidic resistances. However, any suitable parameter of an inlet can be configured.

Additionally or alternatively, the inlet module 116 and the outlet module 107 can include any suitable number of inlets or outlets (e.g., a single sample fluid inlet 117 with a single sheath fluid inlet 118; multiple sample fluid inlets 117 and/or sheath fluid inlets 118; etc.) that carry any suitable fluid (e.g., reagent, buffer, wash, etc.) or component. The inlet(s) 104 and outlet(s) 106 of the substrate 110 can be defined at any suitable end, at any suitable surface, and/or within any suitable region of the substrate no. Other variations of the substrate no can include any other suitable element(s) in any suitable configuration that facilitates coupling with elements external to the substrate no for deforming, processing, and analyzing a sample volume containing particles of interest 102.

3.2 System—Fluidic Pathway

The fluidic pathway 120 functions to provide a path along which particles of interest 102 can travel, be deformed, and/or be analyzed. The fluidic pathway 120 can additionally or alternatively include a first sample fluid branch 124, one or more sheath fluid branches 126, a delivery region 130, a deformation region 140 including an expanding region 144 and/or a narrowing region 142, and/or any suitable formations or regions. Preferably, the fluid channels including the fluidic pathway 120 possess dimensions that facilitate the deformation and analysis of the particles of interest 102. For example, the deformation region 140 can possess a length of 300 µm, with a narrowing region initial upstream width of 30 µm and a narrowing region final downstream width of 15 µm. Alternatively, different dimensions can be used for different fluid channels corresponding to different fluidic pathways 120 (e.g., in different embodiments of the system) in order to accommodate different types of particles of interest 102 (e.g., a first set of fluid channel dimensions for leukocyte applications; a second set of fluid channel dimensions for red blood cell applications; etc.). However, the fluidic pathway 120 can have any suitable, length, width, depth, and/or other dimensions (e.g., described in more detail below).

3.2.A System—Fluidic Pathway—Sample Fluid Branch

The sample fluid branch 124 of embodiments of the fluidic pathway 120 functions to receive and transmit a sample fluid 104 containing the one or more particles of interest 102, to facilitate processing and analysis of the particles 102. Preferably, the sample fluid branch 124 receives and transmits the sample fluid 104, but can additionally or alternatively receive and transmit any other suitable processing fluid. The sample fluid branch 124 is preferably connected to a sample fluid inlet 117 of an inlet module 116 of the substrate 110, and the sample fluid branch 124 preferably receives the sample fluid 104 from the sample fluid inlet 117. Alternatively, the sample fluid branch 124 can be connected to any suitable component, and the sample fluid branch 124 can receive the sample fluid 104 from any suitable component and/or number of components. Preferably, the sample fluid branch 124 transmits the sample fluid 104 to a delivery region 130 of the fluidic pathway 120, but can alternatively transmit the sample fluid 104 to any other region or component. Preferably, the sample fluid branch 124 has a static width (e.g., 20 µm) as the sample fluid 104 progresses along the length of the sample fluid branch 124. Alternatively, the sample fluid branch 124 can have a narrowing width (e.g., an upstream opening width of 20 µm, and a downstream opening width of 15 µm) or an expanding width. The width, length, or depth can also be defined in relation to the width, length, or depth of other suitable components of the fluidic pathway 120 (e.g., specifying the width of the sample fluid branch 124 to be half the width of a sheath fluid branch 126). However, the sample fluid branch 124 can have any suitable dimensions. Preferably, the fluidic pathway 120 includes a single sample fluid branch 124, but can also include any number of branches. The walls of the sample fluid branch 124 are preferably straight, but can be curved, angled, and/or constructed in any suitable orientation for receiving and transmitting the sample fluid 104.

The sample fluid branch 124 can be coupled to the inlet module 116 by a focusing region, as described in U.S. application Ser. No. 14/057,942, where the focusing region is operable to cause the particles 102 of the sample fluid 104 to flow along a set of preferred streamlines in single-file format; however, the sample fluid branch 124 can alternatively be coupled to the inlet module 116 in any other suitable manner. Additionally or alternatively, the sample fluid branch 124 can be configured in any suitable manner.

3.2.B System—Fluidic Pathway—Sheath Fluid Branch

The one or more sheath fluid branches 126 of embodiments of the fluidic pathway 120 functions to receive and transmit a sheath fluid 106. Preferably, the sheath fluid branch 126 receives and transmits the sheath fluid 106 (e.g., including Dextran, methylcellulose, polysorbate, phosphate-buffered saline, alginate, agarose, polyethylene glycol, and/or other suitable components, etc.) but can additionally or alternatively receive and transmit any other suitable processing fluid (e.g., sample fluid 104, buffer, wash, reagent, etc.). The sheath fluid branches 126 are preferably connected to a sheath fluid inlet 118 of an inlet module 116 of the substrate 110, and the sheath fluid branches 126 preferably receive the sheath fluid 106 from the sheath fluid inlet 118. Alternatively, the sheath fluid branches 126 can be connected to any suitable component and/or number of components, and the sheath fluid branch 126 can receive the sheath fluid 106 from any suitable component and/or number of components. Preferably, the one or more sheath fluid branches 126, transmits the sheath fluid 106 to a delivery region 130 of the fluidic pathway 120, but can alternatively transmit the sheath fluid 106 to any other region of component. Preferably, each of the sheath fluid branches 126 has a narrowing width (e.g., an upstream opening width of 30 µm, and a downstream opening width of 25 µm), but can alternatively have an expanding width or static width. The width, length, or depth can also be defined in relation to the width, length, or depth of other suitable components of the fluidic pathway 120 (e.g., a length substantially similar to the length of the sample fluid branch 124). However, the sample fluid branch 124 can have any suitable width, length, or depth, and the width, length, or depth can be static or varying along any dimension. The walls of one or more sheath fluid branches 126 are preferably straight, but can be curved, angled, and/or constructed in any suitable orientation for receiving and transmitting the sheath fluid 106.

Figure 5A:
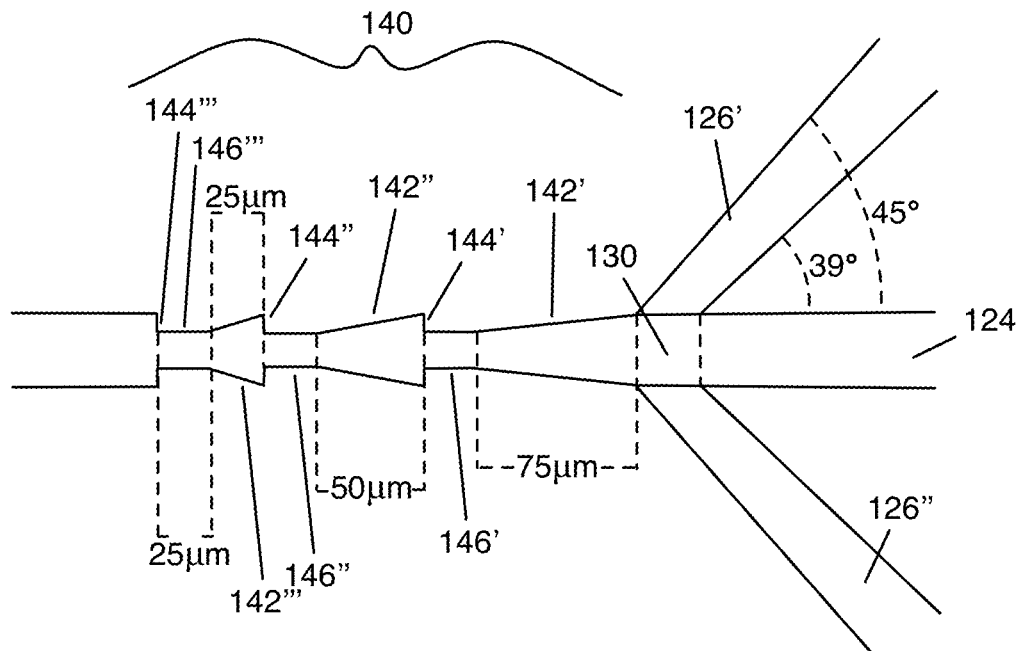
FIGS. 5A-5B are schematic representations of variations of an embodiment of a system for deforming particles.
Figure 5B:
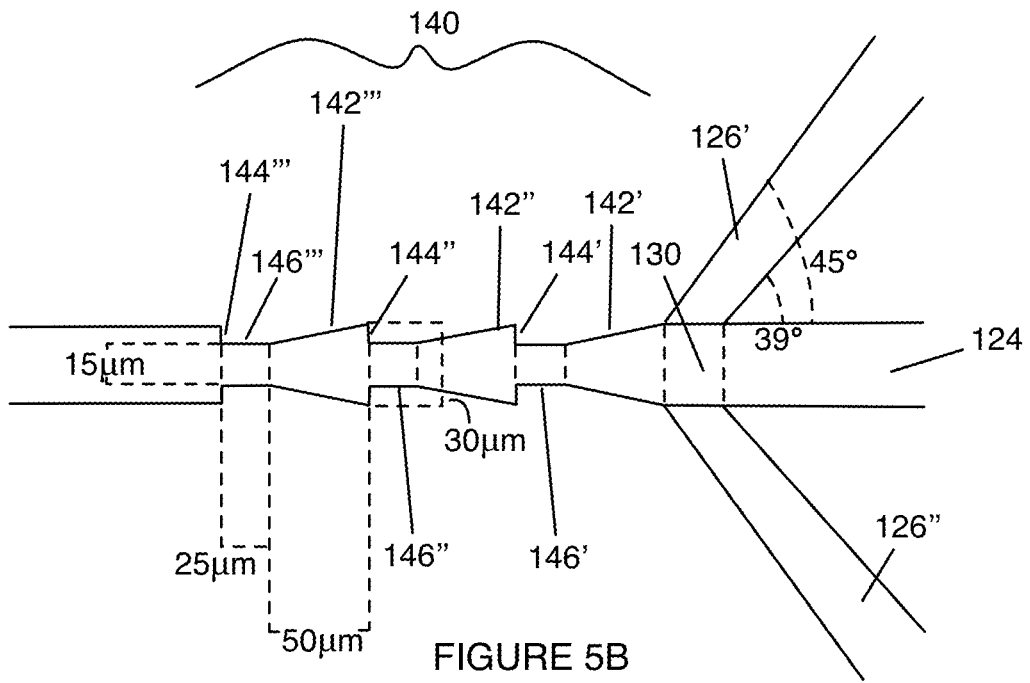

As shown in FIGS. 3 and 5A-5B, the system 100 preferably includes a pair of sheath fluid branches 126 flanking the sample fluid branch 124 on opposing walls along the direction of fluid flow, such that a first sheath fluid branch 126' is positioned to one side of the sample fluid branch 124, and a second sheath fluid branch 126" is positioned to the opposing side of the sample fluid branch 124, but the system 100 can include any number of sheath fluid branches 126. Regions of the fluidic pathway 120 preferably possess a plane of symmetry defined about the longitudinal axis of the sample fluid branch 124, where the one or more sheath fluid branches 126 are symmetric about the plane of symmetry. Alternatively, the sheath fluid branches 126 can be radially symmetric or non-symmetric, but can also be of any orientation with respect to the sample fluid branch 124. Preferably, each sheath fluid branch 126 is non-parallel with the sample fluid branch 124, such that each sheath fluid branch 126 forms an angle with the sample fluid branch 124. As shown in FIGS. 5A-5B, in a first variation, a sheath fluid branch 126 has a narrowing width and the sample fluid branch 124 has a static width, such that an inner angle (e.g., 39 degrees) is defined by the sheath fluid branch wall closest to the sample fluid branch 124, an outer angle (e.g., 45 degrees) is defined by the sheath fluid branch wall farthest from the sample fluid branch 124, and the inner angle and outer angle are different. In an example, the system 100 can include a first sheath fluid branch 126' including a first narrowing fluid channel; and a second sheath fluid branch 126" including a second narrowing fluid channel, where the first and the second narrowing fluid channels substantially symmetrically flank opposing walls of the sample fluid branch 124. In a second variation, the sheath fluid branches 126 and sample fluid branch 124 have a static width (i.e., not narrowing or expanding), such that the angle between a wall of the sample fluid 104 volume and a wall of the sheath fluid branch 126 is the same irrespective of whether the sheath fluid branch wall is the wall closest or farthest from the sample fluid branch 124. However, the sheath fluid branches 126 can be positioned and/or oriented in any suitable fashion in relation to the sample fluid branch 124, other sheath fluid branches 126, other regions of the fluidic pathway 120, walls of the substrate 110, and/or other components or regions of the system 100.

3.2.C System—Fluidic Pathway—Co-Flow

Figure 6A:
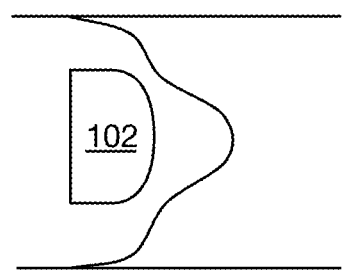
FIGS. 6A-6B are schematic representations of variations of velocity profiles in embodiments of a system and method for deforming particles.
Figure 6B:
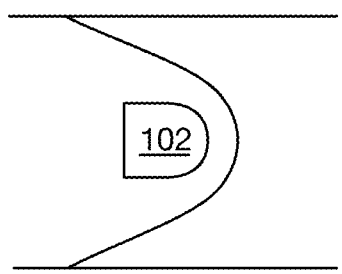

The delivery region 130 and deformation regions 140 of the fluidic pathway 120 preferably facilitate a co-flow between the sample fluid 104 and sheath fluid 106, but the co-flow can include any number or type of a fluids. As shown in FIGS. 6A-6B, velocity profiles for fluid flow through the fluidic pathway 120 can vary, where co-flow (e.g., between the sample fluid 104 and the sheath fluid 106) can result in a velocity profile shown in FIG. 6A, and single flow can result in a velocity profile shown in FIG. 6B. Fluid co-flow can lead to a larger velocity gradient (e.g., resulting in a greater applied forces on the particles 102) as compared to the single flow system, which can facilitate effective drag on the particles 102 and larger morphological changes for better determining measurements of the mechanical properties of the particle. Additionally, fluid co-flow can result in viscous stress enabling increased deformation due to particles 102 being positioned between the multiple streams of fluid in the co-flow along the fluidic pathway 120. In a specific example, 33% of the particle (along the y-axis) can be positioned in the sample fluid 104 at an expanding region 144 (e.g., fluid channel width of 30 μm), and 20% of the particle (along the y-axis) can be positioned in the sample fluid 104 at a narrowing region 142 and/or straight region 146 (e.g., fluid channel width of 15 μm), but any portions of the particle can be in the sample fluid 104 and/or sheath fluid 106 at any given position along the fluidic pathway 120. Applied forces on the particle in a co-flow system can be greater than applied forces in a single flow system by over an order of magnitude, but any suitable applied forces can be generated by the co-flow system. Additionally, forces on the particle (e.g., at an expanding region 144) can generate a differential stress on the particle resulting in a leading edge and a trailing edge viscous force differential that can further deform the particle.

Figure 1:
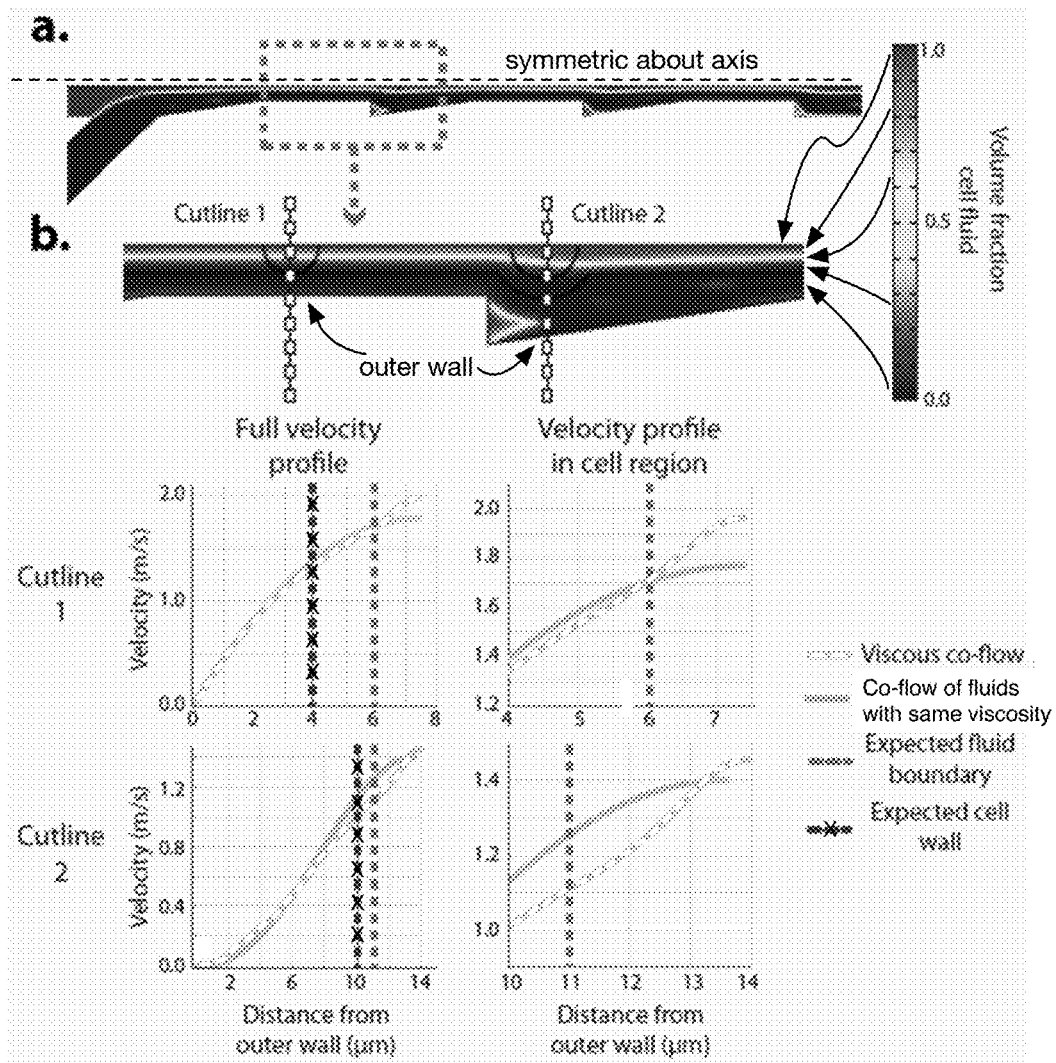
FIG. 1 is a schematic representation of volume fractions and velocity profiles associated with co-flows in embodiments of a system and method for deforming particles.
Figure 2:
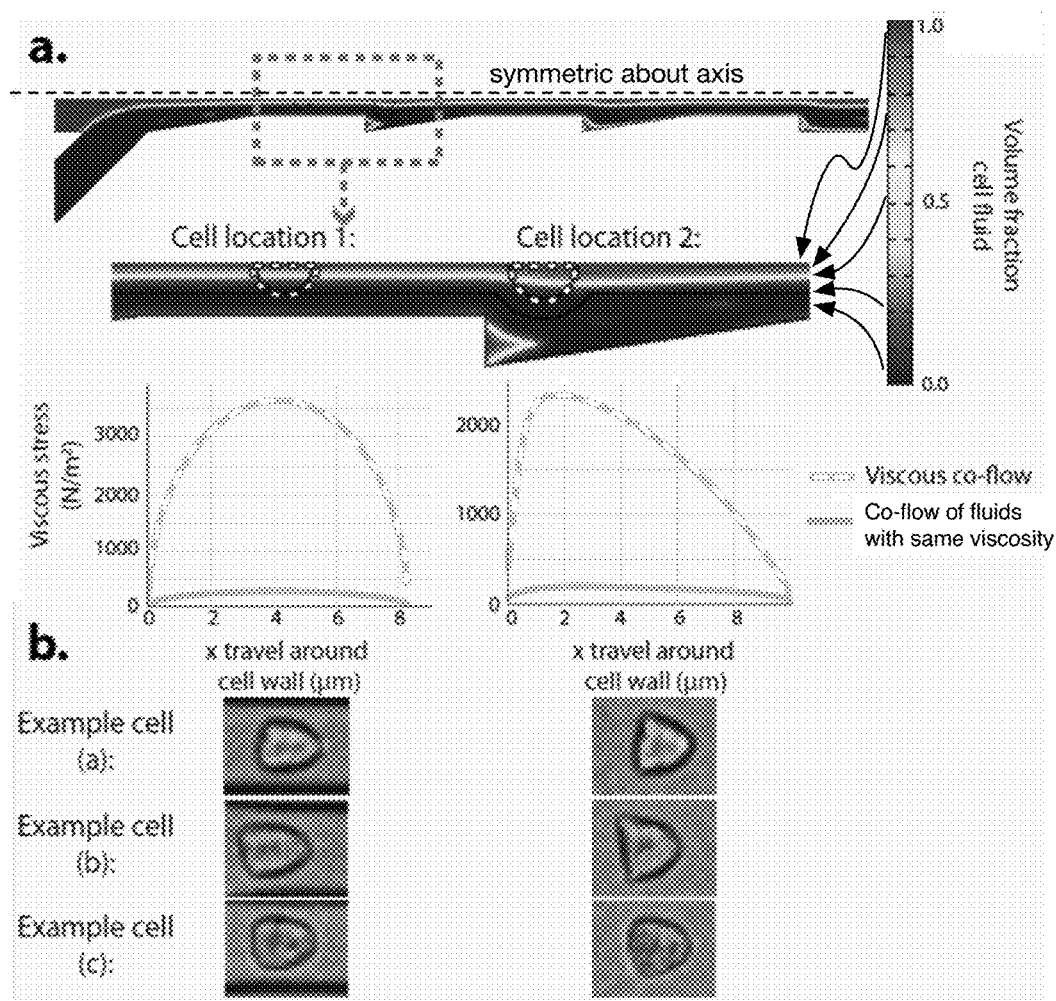
FIG. 2 is a schematic representation of forces on cells or particles in the co-flow, which cause the resultant deformation, in embodiments of a system and method for deforming particles.

The fluids in the co-flow preferably possess different viscosities (e.g., a viscous co-flow), where the different fluid viscosities facilitate a greater velocity gradient relative to a co-flow with fluids of the same or similar viscosity, as shown in FIG. 1; however, each fluid in the co-flow can have any suitable viscosities, compositions, and/or other suitable parameters. In a specific example, as shown in FIG. 1, the greater velocity gradient of the viscous co-flow (e.g., a 1.5-2× greater velocity gradient than a co-flow of fluids with the same viscosity) can be seen by the velocity profiles across a first cutline ("Cutline 1") in a straight region 146 and a second cutline ("Cutline 2") in an expanding region 144 (i.e., where the fluid channel width is wider than the fluid channel width at the first cutline). As shown in FIG. 2, the greater velocity gradient can lead to a greater viscous stress associated with the viscous co-flow relative to a co-flow of fluids of the same viscosity (e.g., a 1-2 order of magnitudes greater viscous stress compared to a same viscosity fluid co-flow).

The different fluids in the co-flow preferably occupy different percentages of a fluid-channel cross-section (e.g., at a given x-position along the fluidic pathway 120). In an example where the co-flow includes a first fluid (e.g., sheath fluid 106) of greater viscosity than a second fluid (e.g., sample fluid 104), the first fluid can occupy a greater percentage of the fluid-channel cross section (e.g., 66%) than the second fluid. In a specific example, at an expanding region 144 where the fluid channel width is 30 μm, the sample fluid 104 can be 4 μm wide (e.g., on average across different leukocytes); however, the dimensions of the fluids in the co-flow can vary based on type of particle. In another specific example, the volume fraction of the sample fluid 104 (e.g., cell fluid) when the sheath fluid 106 and sample fluid 104 of the co-flow are at steady state can be seen in FIG. 1, where the sample fluid 104 is at a viscosity of 1 cP, and the sheath fluid 106 is at a viscosity of 15 cP. However, different fluids in a co-flow can occupy any suitable volumes and/or percentages of the fluid channels (and/or cross-sections of the fluid channels) associated with the fluidic pathway 120, enabling any suitable dimensions of the different fluids in the co-flow.

As shown in FIGS. 1-2, a fluid of lesser viscosity in the co-flow is preferably positioned proximal the center of the fluid channel (e.g., in relation to the width), and a fluid of greater viscosity is preferably positioned along the peripheral of the fluid channel (e.g., in relation to the width, where the fluid of greater viscosity is proximal the fluid channel side walls), but different fluids in the co-flow can be positioned at any suitable locations in relation to the fluid channel. The center of the particles of interest 102 are preferably positioned proximal the center of the fluid channel (e.g., in relation to the width and height), where the center of the particle is preferably in the fluid of lesser viscosity in the co-flow. Further, the peripheral regions of the particle (e.g., distant from the particle center and proximal the fluid channel side walls relative the particle center) are preferably in the fluid of greater viscosity in the co-flow, thereby enabling an increased velocity gradient and increased forces acting on the cell surface. However, portions of the particle can be positioned at any suitable locations in relation to the fluid channel and the fluids of the co-flow.

The co-flow pressures of the fluids (e.g., sample fluid 104 and sheath fluid 106) are preferably matched; however, each fluid can be tuned to have any suitable parameter values (e.g., through tuning of the inlet pressures and the interfacial tension between the fluids). As shown in FIG. 4, the interfacial boundary between the fluids is preferably linear in the fluid channel profile along the z-axis (e.g., an interfacial boundary parallel the z-axis of the fluid channel). A linear interfacial boundary configuration along the z-axis can facilitate a particle center positioned in the fluid of lesser viscosity, and particle peripheral regions positioned in the fluid of greater viscosity (e.g., as the particle travels downstream in the fluidic pathway 120), where such positioning can enable uniform forces applied to the particle of interest along the z-axis (e.g., as opposed to a non-linear interfacial boundary configuration resulting in different forces applied to the particle of interest depending on the z-position), such as at a sub-region of the deformation region 140. Additionally or alternatively, the fluid parameters and interfacial boundaries can be configured in any suitable manner (e.g., curved interfacial boundaries). However, the fluid co-flow and constituent fluids can be otherwise defined.

3.2.D System—Fluidic Pathway—Delivery Region

The delivery region 130 of embodiments of the fluidic pathway 120 functions to receive the sample fluid 104 and the sheath fluid 106, for generating a co-flow (e.g., laminar co-flow) including one or more particles of interest 102. Preferably, the delivery region 130 initiates at a junction between the sample fluid branch 124 and the one or more sheath fluid branches 126. As such, the delivery region 130 is preferably connected to the sample fluid branch 124 and the sheath fluid branches 126. Alternatively, the delivery region 130 can initiate at a junction between any suitable set of branches of the fluidic pathway 120, and the delivery region 130 can be connected to any suitable branch. Preferably, the delivery region 130 is connected to a deformation region 140 of the fluidic pathway 120, and preferably transmits the sheath fluid 106 in a co-flow (e.g., laminar co-flow) with the sample fluid 104 to the deformation region 140. Alternatively, the delivery region 130 can transmit any suitable fluid and/or flow to any suitable region or component of the fluidic pathway 120, with or without co-flow (e.g., laminar co-flow) between fluids in the fluidic pathway 120.

As shown in FIGS. 5A-5B, in one variation, the initiating and terminating regions of the delivery region 130 are defined by the sample fluid branch 124, the sheath fluid branches 126, and the deformation region 140. Preferably, the downstream end of the sample fluid branch 124 defines an initiating region of the delivery region 130, and the upstream end of the deformation region 140 defines a terminating region of the delivery region 130. Preferably, the initiating region and the terminating region are of substantially similar width, and the initiating region and terminating region are preferably substantially parallel. However, the initiating and terminating regions can be of any suitable width in relation to each other (e.g., the initiating region width is 15 μm, and the terminating region width is 20 μm). Preferably, the downstream end of a first sheath fluid branch 126' defines a second initiating region of the delivery region 130, and the downstream end of a second sheath fluid branch 126" defines third initiating region of the delivery region 130. Preferably, the second and third initiating regions are parallel, but can alternatively be non-parallel, curved, and/or of any suitable orientation. Preferably, the perimeter of the delivery region 130 substantially forms a square. However, the delivery region 130 can have any suitable number of sides, the sides of the delivery region 130 can be defined by any suitable region of any suitable component of the fluidic pathway 120, and the delivery region 130 can possess any suitable length(s), width(s), and depth(s). Further, the delivery region 130 can be configured in any suitable manner.

3.2.E System—Fluidic Pathway—Deformation Region

The deformation region 140 of embodiments of the fluidic pathway 120 functions to facilitate deformation of the particles of interest 102. In embodiments, the deformation region 140 can include a series of expanding regions 144, straight regions 146, and/or narrowing regions 142, thereby enabling sequential probing of a particle of interest with decreasing, increasing, or similar forces on the cell over time (e.g., a tunable period of time, such as based on flow rates of the sample fluid 104 and sheath fluid 106). Such configurations can facilitate determination of native viscoelastic properties of the particle of interest by observing the dynamic phase response and fitting the results to mechanical model systems. In an example, the deformation region 140 can include a "tulip" deformation sequence of a narrowing region 142, then a straight region 146, and then an expanding region 144; however, deformation sequences can include any suitable set of regions of the deformation region 140. Multiple tulips can be positioned to follow in sequence of one another (e.g., tulip "A", then tulip "B", then tulip "C"). For example, a first deformation sequence (e.g., a first expanding region 144', first narrowing region 142', and first straight region 146') can be connected to a downstream second deformation sequence (e.g., a second expanding region 144", second narrowing region 142", and second straight region 146"). The degree of deformation of the particle of interest can increase as a particle travels through subsequent "tulips", due to the accumulation of stress over time. "Tulips" of the system can have similar or varying dimensions (e.g., length, width, depth, etc.), and/or any suitable dimensions. However, a "tulip" can be defined for any combination of narrowing regions 142, straight regions 146, and expanding regions 144, and any number of tulips can be included in a deformation region 140. The system 100 can include a single deformation region 140, but can alternatively include any number of deformation regions 140 such as multiple deformation regions 140 in sequence. Preferably, narrowing regions 142, straight regions 146, and/or expanding regions 144 of the deformation region 140 share a longitudinal axis (e.g., coaxial the flow axis for a particle flowing through the fluidic pathway). Alternatively, the longitudinal axes of individual narrowing regions 142, straight regions 146, and/or expanding regions 144 can differ. The longitudinal axis of the deformation region 140 is preferably substantially parallel to and co-linear with the longitudinal axis of the sample fluid branch 124, but can also be non-parallel. However, any axis and/or side of the deformation region 140 can be defined in relation to any axis and/or side of any suitable component of the fluidic pathway 120.

Preferably, the deformation region 140 receives the co-flow (e.g., laminar co-flow) of the sheath fluid 106 and the sample fluid 104 from the delivery region 130, where the co-flow includes the particles of interest 102 to be deformed. Additionally or alternatively, the deformation region 140 can receive the sheath fluid 106 and/or sample fluid 104 from any other suitable region or component of the fluidic pathway 120. The deformation region 140 preferably transmits processed fluid (e.g., the sheath fluid 106 and the sample fluid 104 after deformation of the particles of interest 102) to an outlet of an outlet module 107 of the substrate no. Alternatively, the deformation region 140 can transmit processed and/or unprocessed fluid to any suitable region or component of the fluidic pathway 120.

Preferably, single particles 102 of the particles of interest 102 travel through the deformation region 140 along a set of streamlines forming a substantially single-file line. Alternatively, multiple particles of interest 102 can travel through the deformation region 140 in a manner where multiple particles of interest 102 are positioned at different x-positions in the deformation region 140 at a given time point. A particle of interest can disturb flow lines as the particle of interest travels through the fluidic pathway 120. As such, each particle of interest is preferably separated by at least a minimum distance, where the minimum distance can enable consistent applied forces to be applied to different particles of interest 102 (e.g., of the same type) as they reach a given x-position. However, any suitable particles of interest 102 can be deformed in the deformation region 140 at any suitable time and position.

3.2.E.i System—Fluidic Pathway—Deformation Region—Narrowing Region

The narrowing region 142 of embodiments of the deformation region 140 functions to provide a narrowing fluidic pathway 120 for facilitating the application of fluid stress upon the particles of interest 102. Preferably, a narrowing region 142 of the deformation region 140 is connected to the downstream end of the delivery region 130, such that the co-flow (e.g., laminar co-flow) of the sheath fluid 106 and the sample fluid 104 is transmitted from the delivery region 130 to the narrowing region 142 of the deformation region 140. However, any suitable portion of the deformation region 140 can be connected to any suitable portion of the delivery region 130. Preferably, the narrowing walls of the narrowing region 142 are straight, but can alternatively be curved or any other suitable orientation. Preferably, the initial upstream width of a narrowing region 142 is wider than a final downstream width of the narrowing region 142 (e.g., initial upstream width of 30 µm and final downstream width of 15 µm, as shown in FIG. 5B), but the width of the narrowing region 142 can vary along the region in any suitable fashion to accommodate desired deformation of the particles of interest 102. In a variation, the narrowing region 142 can have a downstream width smaller than a sample fluid branch downstream width of the sample fluid branch 124.

As shown in FIGS. 3 and 5A-5B, in one variation, the deformation region 140 includes multiple narrowing regions 142. Preferably, for a set of narrowing regions 142 (e.g., first, second, and third narrowing regions 142) of a deformation region 140, narrowing regions 142 subsequent to the first narrowing region 142 have their initial upstream opening directly connected to downstream ends of expanding regions 144. For example, a particle of interest traveling through a deformation region 140 could encounter, in sequence, a first narrowing region 142', a first straight region 146', a first expanding region 144', a second narrowing region 142", and multiple subsequent regions. Preferably, an initial upstream width of a narrowing region 142 will be wider than a final downstream width of the narrowing region 142. A given narrowing region 142 will preferably have an initial upstream width and a final downstream width that are substantially similar to the widths of other narrowing regions 142. Alternatively, the initial upstream widths and final downstream widths can vary across the multiple narrowing regions 142. However, the initial upstream widths and final downstream widths can be of any suitable width, and can be defined in relation to any other suitable metric. The deformation region 140 can additionally or alternatively include narrowing regions 142 of varying lengths (e.g., decreasing lengths of narrowing regions 142 along the direction of fluid flow, increasing lengths, decreasing and then increasing lengths, etc.). For example, as shown in FIG. 5A, along the direction of fluid flow, a first narrowing region 142' can have a 75 µm length, a second narrowing region 142" can have a 50 µm length, and a third narrowing region 142'" can have a 25 µm length. However, any narrowing region 142 of the deformation region 140 can possess any suitable width(s), length(s), or depth(s). Further, the deformation region 140 can include any number of narrowing regions 142 configured in any suitable manner.

3.2.E.ii System—Fluidic Pathway—Deformation Region—Expanding Region

The expanding region 144 of embodiments of the deformation region 140 functions to provide an expanding fluidic pathway 120 for facilitating relaxation of the deformation or strain on the particles of interest 102, such as by causing a decrease in velocity at the peripheral regions of the co-flow proximal the expanding fluid channel side walls (e.g., a decrease in velocity of the sheath fluid 106 in a co-flow with sample fluid 104), leading to increased applied forces on the particle peripheral regions positioned in the peripheral regions of the co-flow (e.g., positioned in the sheath fluid 106 proximal the fluid channel side walls) to facilitate determination of native visco-elastic properties of the particle of interest. The deformation region 140 preferably includes multiple expanding regions 144, but can alternatively include only a single expanding region 144. Preferably, the initial upstream width of an expanding region 144 will be less wide than a final downstream width of the expanding region 144 (e.g., an initial upstream width of 30 µm and a final downstream width of 15 µm). In a variation, the expanding region can possess an expanding region maximum channel width (e.g., along the y-axis) greater than a maximum channel width of a pathway region (e.g., straight region, narrowing region, other suitable regions of the fluidic pathway, etc.) upstream (e.g., directly upstream) from the expanding region. In another variation, the expanding region can expand to a final downstream width of 30 µm. The lengths of expanding regions 144 are preferably substantially similar across expanding regions 144 of the deformation region 140, but can alternatively vary across expanding regions 144. However, any expanding region 144 of the deformation region 140 can possess any suitable width(s), length(s), or depth(s). The upstream start of an expanding region 144 is preferably connected to a downstream end of a straight region 146, and the downstream end of an expanding region 144 is connected to an upstream start of a narrowing region 142.

In a first variation, as shown in FIGS. 3 and 5A-5B, the opposing walls of the expanding region 144 along a direction of fluid flow 144 are straight (e.g., having a linear profile of a footprint of the expanding region 144), such that the walls of the expansion region are initially substantially parallel with a longitudinal axis of the deformation region 140, and the walls subsequently angle outwards at the expansion point into a non-parallel orientation with respect to the longitudinal axis of the deformation region 140. For example, as shown in FIGS. 5A-5B, straight walls of an expanding region 144 can initially start as substantially parallel to the longitudinal axis of the deformation region 140, and the walls can then orthogonally angle away from the longitudinal axis (e.g., parallel to the x-axis of the system 100), thus forming orthogonal angles at the expansion point. However, any suitable angle can be formed at the expansion point of the expanding region 144. In a second variation, the expanding walls of the expanding region 144 are curved (e.g., having a non-linear profile of a footprint of the expanding region 144), such that the width expansion is more gradual relative to the example where the expanding walls are straight and form substantially orthogonal angles. For example, a curved expanding wall can form a radius of curvature of a 5 µm, such that the width of the deformation region 140 continues to expand along the x-position of the expanding region 144. For a set of expanding regions 144, a given expanding region 144 can have a different orientation of expanding walls than another expanding region 144. For example, a first expanding region 144 can have straight expanding walls, and a second expanding region 144 can have curved expanding walls. However, the opposing walls of a given expanding region 144 along a direction of fluid flow 144 can be of any suitable orientation, form any suitable angle, and be of any suitable width, length, or depth.

The angle of the expanding region 144 coupled with the flow conditions (e.g. Reynolds number) of the co-flow (e.g., laminar co-flow) are preferably operable to prevent flow separation and vortex formation in the expanding region 144. Such flow separation acts counter to the goal of reducing the stress and relaxing the strain on the deforming particle because the main flow does not decelerate as strongly with separation present. The use of a higher viscosity sheath fluid 106 that is in contact with the walls of the expanding region 144 leads to reduced flow separation by reducing inertial effects locally (i.e. a lower local Reynolds number) for any given flow. This can enable a faster flow of the sample fluid 104 than if the sample fluid viscosity matched with the sheath fluid 106, also leading to higher possible fluid stresses and particle deformations which can be more easily analyzed using imaging approaches. However, the expanding region 144 can be configured in any suitable manner.

3.2.E.iii System—Fluidic Pathway—Deformation Region—Straight Region

The straight region 146 of embodiments of the deformation region 140 functions to provide a static-width region of the fluidic pathway 120 for facilitating deformation of particles of interest 102. Preferably, the deformation region 140 includes multiple straight regions 146, but can alternatively include only a single straight region 146. The initial upstream width of a straight region 146 is preferably substantially similar to the final downstream width of a straight region 146, and the length of the straight region 146 is preferably configured (e.g., at greater than 25 μm) for facilitating stressing of particles of interest 102. In a variation, the straight region 146 possesses a static width substantially equivalent to the downstream width of a narrowing region 142. However, straight regions 146 of the deformation region 140 can have any suitable width(s), length(s), and depth(s). Preferably, the opposing walls of a straight region 146 along a direction of fluid flow 146 are substantially straight, but can alternatively be curved or of any other suitable orientation. The upstream region of a given straight region 146 is preferably connected to a downstream end of a narrowing region 142, and the downstream end of a given straight region 146 is preferably connected to an upstream region of an expanding region 144. However, sequences of narrowing regions 142 and expanding regions 144 can alternatively be configured in any other suitable manner. For example, for a particle of interest traveling through a deformation region 140, the particle of interest can encounter, in sequence, multiple sequences in series of a narrowing region 142, then a straight region 146, and then an expanding region 144. Further, straight regions 146 can be configured in any suitable manner.

3.3 Heating Element, Pressurizing Element

The system 100 can additionally or alternatively include a heating element, which functions to adjust the temperature of fluid traveling through the fluidic pathway 120, and the system can additionally or alternatively include a pressurizing element, which functions to adjust the pressure level of the fluid traveling through the fluidic pathway 120. Preferably, the heating and/or pressurizing element is modular with the substrate 110, such that the heating and/or pressurizing element can be detached or re-attached to the substrate 110. Alternatively, the heating and/or pressurizing element can be integrally constructed (e.g., physically coextensive, of unitary construction) with components of the system 100. Preferably, the heating and/or pressurizing element can adjust the temperature and/or pressure level at specific regions of the substrate 110 and/or fluidic pathway 120. For example, the heating element can focus heating to the deformation region 140 of the fluidic pathway 120 to facilitate a desired temperature of fluid traveling through the deformation region 140. However, the heating and/or pressurizing element can adjust the temperature and/or pressure level in any suitable fashion (e.g., uniformly) to any suitable portions of the system 100.

4. Method

Figure 9:
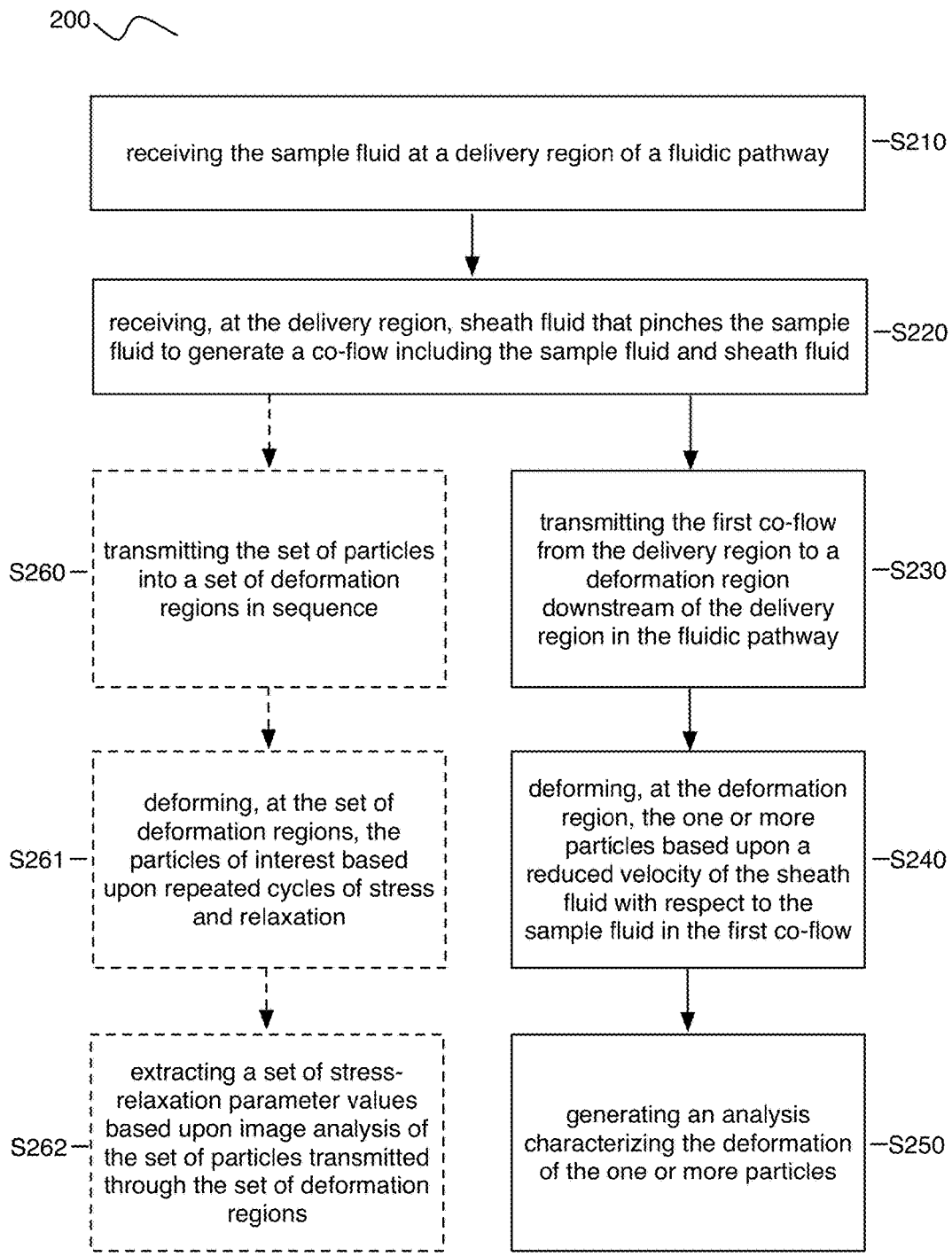
FIG. 9 is a flow chart of embodiments of a method for deforming particles.

As shown in FIG. 9, an embodiment of a method 200 for deforming one or more particles from a set of particles of a sample fluid includes receiving the sample fluid at a delivery region of a fluidic pathway S210; receiving, at the delivery region, sheath fluid that pinches the sample fluid to generate a co-flow including the sample fluid and sheath fluid S220; transmitting the co-flow from the delivery region to a deformation region downstream of the delivery region in the fluidic pathway S230; deforming the particle at the deformation region based upon a reduced velocity of the sheath fluid with respect to the sample fluid in the co-flow S240; and generating an analysis characterizing the deformation of the one or more particles S250.

In some variations, the method can additionally or alternatively include transmitting the set of particles into a set of deformation regions in sequence S260, deforming, at the set of deformation regions, the particles of interest based upon repeated cycles of stress and relaxation S261, and extracting a set of stress-relaxation parameter values based upon image analysis of the set of particles transmitted through the set of deformation regions S262.

One or more instances of the method 200 and/or processes described herein can be performed asynchronously (e.g., sequentially), concurrently (e.g., in parallel) and/or in any other suitable order at any suitable time and frequency by and/or using one or more instances of the system 100, components of the system 100, and/or entities described herein. Additionally or alternatively, aspects described in relation to the method 200 can be applied to any suitable types of fluid.

4.1 Method—Receiving a Sample Fluid

Block S210 recites: receiving the sample fluid at a delivery region of a fluidic pathway, and functions to receive a sample fluid including one or more particles of interest, to initiate processing and analysis of the one or more particles. Preferably, the sample fluid is received from a sample fluid branch connected to a sample fluid inlet of an inlet module of the substrate. However, the sample fluid can be received from any suitable component. The sample fluid is preferably received at the delivery region defining a junction between the sample fluid branch and one or more sheath fluid branches but the sample fluid can be received at any suitable embodiment of a delivery region described above. The width of the sample fluid is preferably substantially static in the fluid channel profile along the z-axis, which can facilitate uniform forces applied to the particle along the fluid channel z-axis, but the sample fluid width can alternatively vary in the fluid channel profile along the z-axis.

Regarding Block S210, preferably, the sample fluid is received at the delivery region and associated with a particle stream fluid velocity that is adjustable (e.g., between sample runs, such as by varying flow rate associated with the fluid delivery module). For example, a specific flow rate (e.g., 25 μL/min) or a flow rate range (e.g., 5 μl/min to 50 μl/min) can be configured (e.g., by the fluid delivery module). Additionally or alternatively, the method 200 can include adjusting a particle stream velocity (e.g., 0.2 m/s) observed at the delivery region. The viscosity of the sample fluid is preferably less than the viscosity of the sheath fluid (e.g., sample fluid viscosity of 1 cP and sheath fluid viscosity of 15 cP, as shown in FIG. 1), but the fluids in the co-flow can have any suitable viscosities. Additionally or alternatively, any suitable parameter of the sample fluid can be configured. However, Block S210 can be performed in any suitable manner.

4.2 Method—Receiving a Sheath Fluid

Block S220 recites: receiving, at the delivery region, a sheath fluid to generate a co-flow (e.g., laminar co-flow) (e.g., with the sample fluid) including one or more particles from the set of particles, and functions to receive a sheath fluid to facilitate deformation and analysis of the one or more particles. Preferably, the sheath fluid is received from one or more sheath fluid branches flanking a sample fluid branch (e.g., a pair of sheath fluid branches), where the delivery region is defining a junction between the sample fluid branch and sheath fluid branches. However, the sheath fluid can be received from any suitable component. The sheath fluid preferably sheaths the sample fluid (e.g., at two or more opposing sides; at peripheral regions of the sample fluid proximal the fluid channel side walls; etc.), but can sheath any suitable fluid. Fluids in the co-flow can have any suitable amount of mixing. At the delivery region, the particles of interest preferably undergo enhanced deformation based upon the interaction of the sheath fluid with the sample fluid. However, the sheath fluid can interact with the sample flow in any suitable fashion, influencing the particles of interest in any suitable manner.

Regarding Block S220, preferably, various parameters associated with the sheath fluid (e.g., flow rate, sheath fluid stream velocity, viscosity, etc.) can be adjusted, but any other suitable parameter can be configured. Various parameters relating to the flow of the sheath fluid and/or sample fluid can be predetermined, user-determined, learned (e.g., based on the type of particle, sheath fluid, sample fluid, etc.), dynamically calculated (e.g., maintaining sheath fluid velocity above a certain threshold during a sample run), and/or determined in any suitable manner. Preferably, the stream velocities associated with receiving the sample fluid and the sheath fluid can be varied in relation to one another. In an example, the method 200 can include tuning the sample fluid and/or sheath fluid parameters to achieve a particle stream average velocity of 2 m/s (e.g., for leukocytes), but any suitable particle stream average velocity can be obtained (e.g., for different types of particles). In another example, parameters associated with the sheath fluid can be tuned to vary a sheath fluid stream average velocity (e.g., across a deformation region; across the sheath fluid branch; across the overall fluidic pathway; etc.), such as while statically fixing the particle stream average velocity (e.g., across a deformation region; across the sheath fluid branch; across the overall fluidic pathway; etc.). In another example, a pinch velocity can be defined for the received sample fluid and sheath fluid, where the pinch velocity can be a ratio of the sheath fluid stream average velocity over the particle stream average velocity (e.g., across the entire deformation region; an expanding region; a narrowing region; other suitable portions of the fluidic pathway and/or fluid channels; etc.). In another example, the method 200 can include tuning parameters to adjust the velocity profiles illustrated in FIG. 1. In other examples, the method can include maintaining a ratio of a flow rate of the sheath fluid in relation to a flow rate of the sample fluid (e.g., maintaining, over time with the fluid delivery module, a 10:1 flow rate ratio for the sheath fluid relative to the sample fluid). In further examples, different particle sizes can be accommodated by tuning sheath fluid parameters, sample fluid parameters, and/or other suitable parameters to modify sheath characteristics in relation to sample fluid characteristics, and vice versa, in order to induce deformation at specific regions of a given particle (e.g., peripheral regions proximal the fluid channel walls). For example, the method 200 can include tuning sheath fluid parameters (e.g., while keeping sample fluid width constant, such as at an average width of 4 μm at an expanding region associated with a fluid channel width of 30 μm) to modify particle velocity at a given x-position along the fluidic pathway, where such parameters can be tailored for different types of particles. In another example, the method 200 can include tuning a sample fluid width to accommodate differences in particle size. In a specific example, the method 200 can include: prior to receiving the sample fluid and the sheath fluid at the delivery region, tuning a first set of parameters for at least one of the sample fluid and the sheath fluid based on a first particle size of a first particle, to facilitate a tri-humped velocity profile (e.g., having a plurality of inflection points) of a first co-flow at the deformation region; tuning a second set of parameters for a second co-flow (e.g., in a second sample run) including a second particle, based on a second particle size of the second particle; and deforming the second particle at the deformation region based on the second set of parameters, to facilitate a tri-humped velocity profile of the second co-flow. However, any suitable velocity profile having any suitable number of inflection points can be facilitated.

In one variation of Block S220, fluid and flow parameters can be adjusted to achieve desired profiles (e.g., velocity profile, pressure profile, concentration profile, streamline profile, etc.) at the delivery region and/or the upstream start of the deformation region. In a first example, pinch velocity and fluid viscosity can be adjusted to achieve a desired flow stream stability, such as a tighter and more consistent streamline profile without vortices as the fluid progresses downstream along an x-axis of the fluidic pathway. In a second example, sheath fluid flow rate in relation to sample fluid flow rate can be adjusted to achieve a desired profile shape of fluid dynamic parameters (e.g., a triangular velocity gradient vs. a tri-humped velocity gradient, etc.). However, Block S220 can be performed in any suitable manner.

4.3 Method—Receiving the Co-Flow

Block S230 recites: transmitting the first co-flow from the delivery region to a deformation region downstream of the delivery region in the fluidic pathway, and functions to receive a co-flow (e.g., laminar co-flow) at the deformation region to facilitate deformation and analysis of the particles of interest. Preferably, substantially proximal to the upstream start of the deformation region, the co-flow (e.g., laminar co-flow) possesses a tri-humped velocity profile. However, the co-flow (e.g., laminar co-flow) can possess any suitable velocity profile and/or pressure profile for suitably deforming the particles of interest. Preferably, the co-flow (e.g., laminar co-flow) includes the one or more particles of interest, and the particles preferably travel through the deformation region along a set of streamlines in a substantially single-file line, such that individual particles can be deformed and analyzed in a uniform manner, but any number of particles can simultaneously be processed for any given x-position and time stamp. A characteristic thickness of the sheath fluid flow surrounding the sample fluid flow provides enhanced localized deformation at one or more particle peripheral regions (e.g., distant from the particle center; proximal the fluid channel side walls; regions of the particle in the sheath fluid of the co-flow; etc.). Alternatively, the co-flow (e.g., laminar co-flow) can possess any suitable flow behavior. Fluid and flow parameters can preferably be adjusted to achieve a desired co-flow behavior (e.g., laminar flow), but any suitable parameter can be adjusted to achieve any suitable flow characteristic. Preferably, the co-flow (e.g., laminar co-flow) is received from the delivery region, and the co-flow is preferably received at a narrowing region of the deformation region. Additionally or alternatively, the co-flow can be received from any suitable structural element, and can be received at any suitable region (e.g., narrowing region, expanding region, straight region, etc.) of the deformation region. However, Block S230 can be performed in any suitable manner.

4.4 Method—Deforming Particles of Interest

Block S240 recites: deforming, at the deformation region, the one or more particles based upon a reduced velocity of the sheath fluid with respect to the sample fluid in the co-flow (e.g., laminar co-flow), and functions to apply or remove fluid dynamic stress on the one or more particles in facilitating analysis of deformation characteristics of the particles of interest. Preferably, as the co-flow (e.g., laminar co-flow) travels through the deformation region, such that for a given x-position along the longitudinal axis of the deformation region, the viscosity in the co-flow fluid near the walls of the fluidic channel is increased as compared to the viscosity of the co-flow fluid at the center of the flow. Alternatively, the co-flow can have any suitable viscosity profile for facilitating controlled deformation of the particles. Preferably, the co-flow velocity gradient and fluid dynamic stress and strain is enhanced in magnitude compared to a uniform viscosity profile across the surface of the one or more particles for a given x-position along the longitudinal axis of the deformation region, but the co-flow velocity profile can be any suitable profile for facilitating desired deformation characteristics. A difference in velocities of the fluids in the co-flow (e.g., facilitated by the differences in viscosities of the fluids and the changing width of the fluid channel at the deformation region) can lead to a pinching of the co-flow by the higher viscosity fluid (e.g., a sheath fluid), which can facilitate, for example, interaction between the higher viscosity fluid and the particle peripheral regions (e.g., the particle boundaries proximal the fluid channel side walls, etc.) when the particle diameter spans beyond the sample fluid region of the co-flow, and while the particle center is positioned in the fluid of smaller viscosity (e.g., sample fluid). As shown in FIGS. 1 and 6A, for example, fluid and flow parameters can be adjusted to achieve a velocity profile of the co-flow where velocity is reduced proximal the peripheral regions of a particle of interest, and where the velocity profile has a downstream-facing protrusion substantially centered between the opposing walls along a direction of fluid flow. This flow profile with respect to the particle can yield a higher viscosity fluid interacting with the particle boundary and a higher shear rate, both of which cooperate to yield a higher surface stress acting on the particle and larger, more visible deformation Alternatively, as shown in FIG. 6B, the velocity profile can omit the downstream-facing protrusion and follow a parabolic-like profile. However, fluid and flow parameters can be adjusted in any suitable fashion to achieve any suitable profile.

Figure 8A:
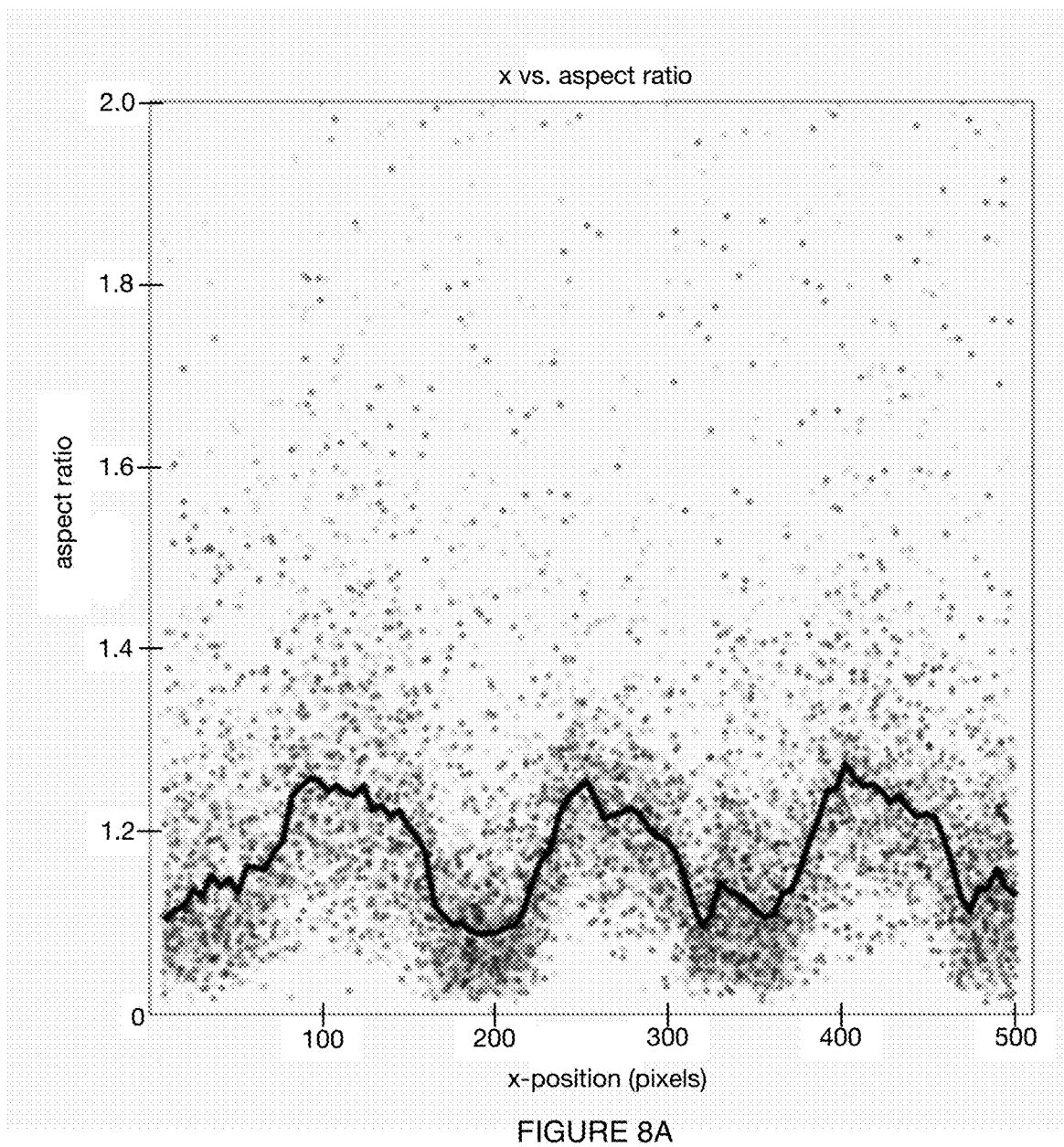
FIGS. 8A-8B illustrate variations of deformation metrics in embodiments of a system and method for deforming particles.
Figure 8B:
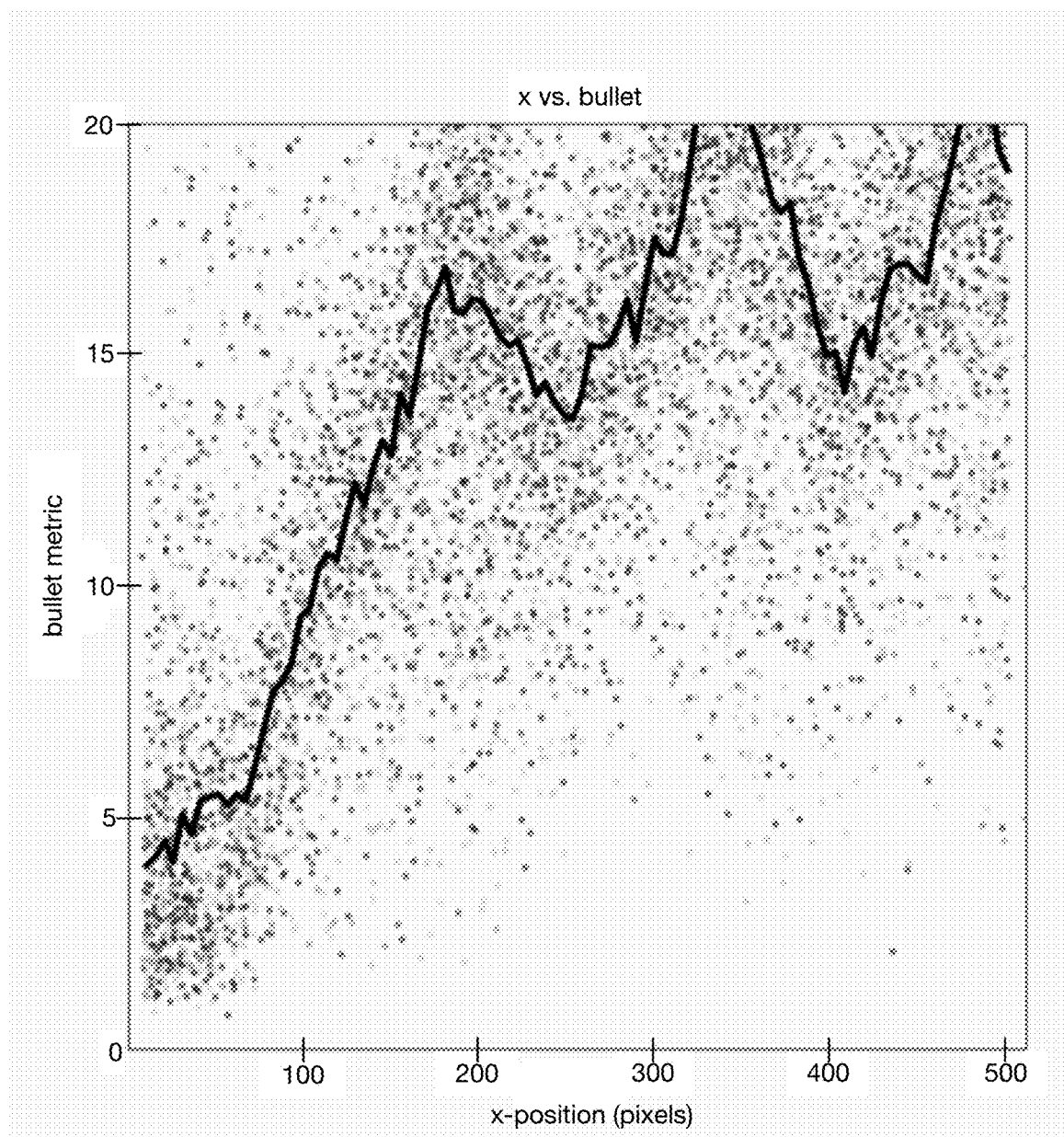

Regarding Block S240, preferably, deformation metrics can be measured to characterize the deformation of the particles as the particle travels along the deformation region. As shown in FIGS. 8A-8B, examples of deformation metrics include: bullet shape metric (e.g., a measure of similarity between particle shape and an asymmetric shape of a bullet, such as by measuring a triangular aspect ratio through the centroid of a cell, as shown in FIG. 8B), aspect ratio, and/or any other suitable parameter characterizing deformation of the particle (e.g., circularity).

Block S240 can include calculating a bullet metric based on an optical dataset of the particle in the deformation region. Calculating the bullet metric can include: determining a trace the particle wall represented in the optical dataset; translating the trace into polar coordinates (e.g., from x-y coordinates derived from the optical dataset); and determining a harmonic (e.g., third harmonic) of a discrete Fourier transform of the polar trace. Calculating the bullet metric can additionally or alternatively include normalizing for cell size (e.g., by dividing the third harmonic by the zeroth harmonic of the discrete Fourier transform); multiplying by a multiplication factor (e.g., a multiplication factor of 100; to facilitate visual display of the data; etc.), and/or other suitable operations.

In relation to Block S240, preferably, fluid and flow parameters can be adjusted to achieve a large peak-trough difference in bullet metric, circularity, and aspect ratio as a function of x-position along the deformation region. However, fluid and flow parameters can be adjusted to achieve any sort of characteristic of a deformation metric. In one variation, deforming the particles of interest includes cycling particles of interest through phases of strain and relaxation as the particles of interest travel along the deformation region. Preferably, the particles of interest cycle through high stress phases that lead to strain (deformation) as well as low stress phases that lead to relaxation (e.g., back to an initial particle shape), but deforming the particles can alternatively only include a single high stress phase. Preferably, the particles of interest undergo a compressive stress phase as the particles of interest travel through a narrowing region, and undergo an asymmetric viscous stress causing a magnified bullet-like shape as the particle of interest travel through an expanding region. Alternatively, strain and relaxation of the particles can occur at any suitable region of the deformation region and/or fluidic pathway. As shown in FIGS. 8A-8B, given the cycles of stress and relaxation, values of the bullet metric, aspect ratio, and/or other deformation parameters for a particle of interest can go through cycles of peaks and troughs as a function of x-position along the deformation region. In examples, for a given particle of interest, the x-position for a peak or trough can vary based on the type of deformation metric evaluated, where the x-positions corresponding to peaks or troughs can map to specific regions of the deformation region (e.g., peak bullet metric as the particle enters an expanding region, and a peak aspect ratio when the particle is in a narrowing region). As shown in FIGS. 8A-8B, the x-position for the first peak of the bullet metric is staggered (e.g., at a later x-position) compared to the x-position for the first peak of the aspect ratio. Determining deformation metrics can be for a single particle, for a population of particles, and/or for any suitable subgroup of particles. Additionally or alternatively, deformation parameters can display any suitable behavior in relation to deformation of the particles of interest. However, any type of force can be applied to the particles of interest at any suitable region in order to achieve any suitable deformation characteristic, and Block S240 can be performed in any suitable manner.

4.5 Method—Generating an Analysis

Block S250 recites: generating an analysis characterizing the deformation of the one or more particles, and functions to characterize the particles of interest. Generating the analysis preferably includes collecting morphology data for the particles of interest as the particles travel through the fluidic pathway (e.g., the deformation region of the fluidic pathway). Collecting morphology data can include capturing an optical dataset (e.g., images) of the particles with a morphology data collection system, which can include an optical system (e.g., a high-speed camera capturing images at 200,000-500,000 frames per second; a high-speed camera capturing images at 100,000-200,000 frames per second for a system configured to trigger image capture in response to detecting a particle in the field of view of the camera; etc.) and/or other suitable components; transforming the optical dataset into a morphology dataset; and/or other suitable operations. However, determining a morphology dataset can be performed in any suitable manner, such as in a manner analogous to that described in U.S. application Ser. No. 14/057,942, entitled "SYSTEM AND METHOD FOR DEFORMING AND ANALYZING PARTICLES" and filed on 18 Oct. 2013, which is incorporated herein in its entirety by this reference. Generating the analysis is preferably based on the collected morphology dataset, but can additionally or alternatively be based on any suitable dataset. Block S250 is preferably implemented at embodiments of the morphology data collection system and the processor described above; however, Block S250 can additionally or alternatively be performed using any suitable components operable to generate an analysis based upon a suitable dataset. In variations, the processor can include a first module that extracts a set of deformation characteristics from a morphology dataset; and a second module operable to generate the analysis. As such, Block S250 can further include Block S251, generating a morphology dataset characterizing deformation of the particles within the deformation region. Additionally or alternatively, the processor can include a third module that extracts a set of fluorescence parameters from a fluorescence dataset; and/or a fourth module operable to synchronize the morphology dataset and the fluorescence dataset based upon a deformation characteristic and a fluorescence parameter.

Figure 7:
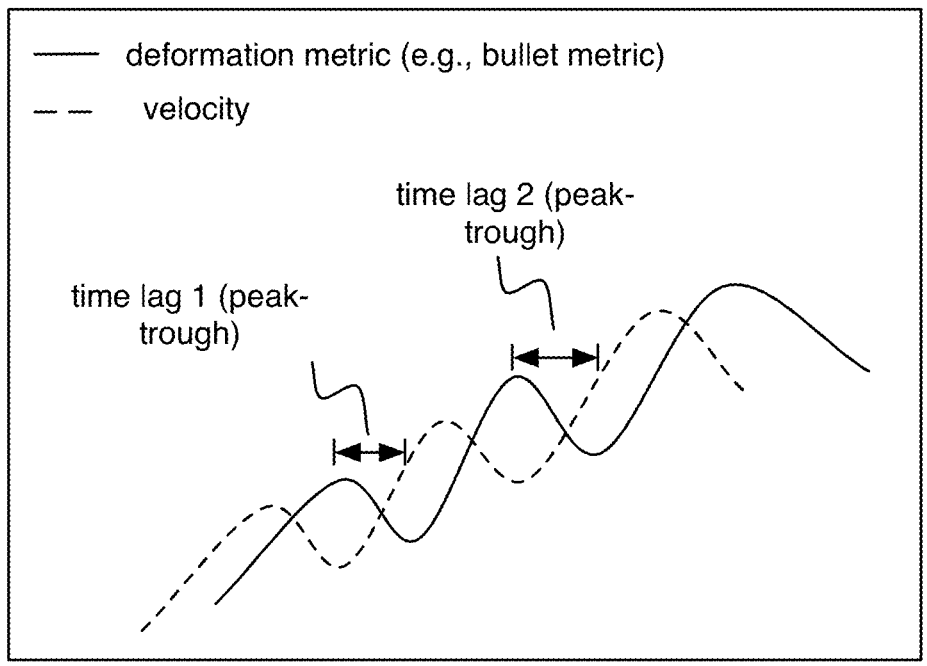
FIG. 7 is a schematic representation of a deformation metric and velocity as a function of time in embodiments of a system and method for deforming particles.

Regarding Block S250, as shown in FIG. 10, in one variation, deformation characteristics of particles of interest (e.g., phorbol myristate acetate-treated and -untreated leukocytes; etc.) can be extracted from analyzing a captured deformation metric as a function of time (and x-position as the particle travels through the fluidic pathway). For example, measuring the duration of cell bulleting or cell relaxation can illuminate characteristics of about the mechanical properties of a particular cell. In another example, Block S250 can include determining a series a deformation metrics as a function of particle x-position along the fluidic pathway, where the series of deformation metrics includes a series of peaks and troughs associated with x-positions corresponding to repeated cycles of stress and relaxation applied to the particle (e.g., a leukocyte, where the method 100 can include characterizing a sepsis-related condition based on a correlation between the sepsis-related condition and the series of peaks and troughs). In another example, the method 200 can include tuning deformation metric parameters as a function of time based on viscosity of fluids in the co-flow (e.g., where viscosities associated with the co-flow can modify the rate of deformation and/or relaxation). In another example, Block S250 can include assessing a time lag, which can include: the time between peaks and troughs for velocity over time and deformation metric over time (e.g., as shown in FIG. 7 for velocity and bullet metric); time between a first deformation metric condition and a second deformation metric condition (e.g., time between a bullet metric peak and a bullet metric trough, time between the start of an initial expansion etc.); and/or any other suitable time lag between any suitable measurements. In another example, deformation metrics as a function of time (and/or any suitable deformation metric) can be compared between different types of particles of interest (e.g., leukocytes versus red blood cells), which can illuminate the relative viscous characteristics between particles of interest. However, any suitable characteristic about any suitable particle of interest can be extracted from generating an analysis, and Block S250 can be performed in any suitable manner.

4.6 Method—Variations

In some variations, the method 200 can additionally or alternatively include Block S260, transmitting the set of particles into a set of deformation regions in sequence; Block S261, deforming, at the set of deformation regions, the particles of interest based upon repeated cycles of stress and relaxation; Block S262, extracting a set of stress-relaxation parameter values based upon image analysis of the set of particles transmitted through the set of deformation regions; and/or other suitable operations.

Block S260 recites: transmitting the set of particles into a set of deformation regions in sequence, and functions to deliver one or more particles of interest into a plurality of deformation regions positioned in series (e.g., expanding regions connected to narrowing regions, etc.) along the fluidic pathway. Preferably, each deformation region is composed of the same pattern of one or more narrowing regions, straight regions, and expanding regions. For example, a deformation region can be defined as a narrowing region, followed by a straight region, and followed by an expanding region. Such deformation regions can be placed in sequence, one after another, such that two deformation regions placed in sequence would include, in sequential order: a first narrowing region, a first straight region, a first expanding region, a second narrowing region, a second straight region, and a second expanding region. However, a deformation region can be composed of any suitable combination of any suitable type of region.

Block S261 recites: deforming, at the set of deformation regions, the particles of interest based upon repeated cycles of stress and relaxation, and functions to apply cycles of stress and relaxation to the one or more particles of interest in facilitating analysis of deformation characteristics of the particles. Preferably, for a given particle of interest traveling through a deformation region, the stress state of the particle is greater at the end of the deformation region than at the beginning. Alternatively, the stress states at the start and end of the deformation region can be substantially similar or relate to one another in any suitable manner.

Block S262 recites: extracting a set of stress-relaxation parameter values based upon image analysis of the set of particles transmitted through the set of deformation regions, and functions to capture deformation characteristics of the particles of interest. Preferably, extraction of the stress-relaxation parameter values and analyzing images of the set of particles is performed by the detection module described above, but Block S272 can be performed by any suitable entity. Preferably, sets of stress-relaxation parameter values can be extracted for the particle of interest at any suitable timeframe and/or at any suitable x-position along the deformation region. Stress-relaxation parameter values preferably include the deformation parameters described above, but can also include any other additional parameter values describing the stress and relaxation characteristics of the particles of interest, such as peak "bulleting" parameters (e.g., parameters characterizing the deformation of the particle when the particle most embodies "bulleting" characteristics), deformation parameters at specific positions of the deformation region (e.g., at an expanding region, narrowing region, straight region, etc.), final relaxation parameters (e.g., characterizing a particle relaxation after the particle travels through the deformation region, subsequent to the deformation region) and/or any other suitable parameters. As shown in FIG. 2, "bulleting" characteristics can result from the underlying shape of the flow field in the co-flow (e.g., laminar co-flow) surrounding a particle, and in particular, a relatively slower flow velocity of the co-flow fluid interfacing with peripheral regions of the particle (e.g., distant from the particle center; proximal the fluid channel side walls; regions of the particle in the sheath fluid of the co-flow; etc.) compared to the particle stream velocity, yielding a unique distribution of fluid stresses acting on the particle surface. Preferably, the index of refractions of the sheath fluid and the sample fluid can be adjusted (e.g., substantially matching index refractions) for facilitating image capture of the deformation of the particles, where the index of refractions of fluids in the co-flow can be tuned to reduce a lensing effect that can vary depending on the z-axis profile of the co-flow (e.g., z-axis profile of the interfacial boundary between fluids in the co-flow), and/or fluids in the co-flow. However, any other fluid or flow parameter can be adjusted to facilitate image analysis and extraction of stress-relaxation parameter values. Preferably, one or more of the parameters can be extracted from the time-dependent data according to viscoelastic models (e.g., spring and dashpot models), but can alternatively be extracted using any other suitable model. However, Blocks S260-S262 can be performed in any suitable manner.

The method 200 can, however, include any other suitable steps or combination of steps that facilitate the deformation, assaying, and/or analysis of particles of a sample volume. Further, any suitable system 100 component can perform any suitable step or combination of steps of method 200. As a person skilled in the art will recognize from the previous detailed description and from the figures and claims, modifications and changes can be made to the embodiments of the method 200 without departing from the scope of the method 200.

The FIGURES illustrate the architecture, functionality and operation of possible implementations of systems, methods and computer program products according to preferred embodiments, example configurations, and variations thereof. In this regard, each block in the flowchart or block diagrams can represent a module, segment, step, or portion of code, which includes one or more executable instructions for implementing the specified logical function(s). It should also be noted that, in some alternative implementations, the functions noted in the block can occur out of the order noted in the FIGURES. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions. The system 100 and method 200 include every combination and permutation of the various system components and the various method processes, including any variations, embodiments, examples, and specific examples.

The system 100 and/or method 200 of the embodiments can be embodied and/or implemented at least in part as machine operable to receive a computer-readable medium storing computer-readable instructions. The instructions are preferably executed by computer-executable components preferably integrated with the system and one or more portions of the processor and/or analysis engine. The computer-readable medium can be stored in the cloud and/or on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the embodiments of the invention without departing from the scope of this invention defined in the following claims.

We claim:

1. A method for characterizing deformation of a first particle in a sample fluid, the method comprising:
   receiving the sample fluid at a delivery region of a fluidic pathway;
   receiving a sheath fluid at the delivery region of the fluidic pathway, wherein the sheath fluid pinches the sample fluid to generate a first co-flow comprising the sheath fluid and the sample fluid;
   transmitting the first co-flow from the delivery region to a deformation region downstream of the delivery region in the fluidic pathway;
   deforming the first particle at the deformation region based upon a change in velocity of the sheath fluid with respect to the sample fluid in the first co-flow, wherein deforming the first particle comprises applying an increased stress on particle peripheral regions positioned in the sheath fluid of the first co-flow at the deformation region;
   capturing an optical dataset of the first particle traveling through the deformation region; and
   determining a morphology dataset describing the deformation of the first particle at the deformation region based on the optical dataset;
   wherein the sheath fluid possesses a sheath fluid viscosity greater than a sample fluid viscosity of the sample fluid, and wherein the first particle center is positioned in the sample fluid of the first co-flow at the deformation region.

2. The method of claim 1, wherein deforming the first particle at the deformation region comprises applying repeated cycles of stress and relaxation to the first particle, wherein transforming the optical dataset into a morphology dataset comprises determining a series a deformation metrics as a function of particle x-position along the fluidic pathway, and wherein the series of deformation metrics comprises a series of peaks and troughs associated with x-positions corresponding to the repeated cycles of stress and relaxation.

3. The method of claim 2, wherein the first particle is associated with leukocytes, and wherein the method further comprises characterizing a sepsis-related condition based on a correlation between the sepsis-related condition and the series of peaks and troughs of the series of deformation metrics.

4. The method of claim 2, wherein applying repeated cycles of stress and relaxation to the particle comprises transmitting the first co-flow through a series of expanding regions connected to narrowing regions of the deformation region.

5. The method of claim 1, wherein the first particle possess a first particle size, and wherein the method further comprises: prior to receiving the sample fluid and the sheath fluid at the delivery region, tuning a first set of parameters for at least one of the sample fluid and the sheath fluid based on the first particle size, to facilitate a tri-humped velocity profile of the first co-flow at the deformation region.

6. The method of claim 5, further comprising:
tuning a second set of parameters for a second co-flow comprising a second particle, based on a second particle size of the second particle; and
deforming the second particle at the deformation region based on the second set of parameters, to facilitate a tri-humped velocity profile of the second co-flow.

7. The method of claim 1, wherein the co-flow at the deformation region comprises a substantially linear co-flow interfacial boundary along the z-axis.

8. The method of claim 7, wherein the sheath fluid occupies a greater percentage of the fluidic pathway than the sample fluid at the sub-region of the deformation region.

9. The method of claim 1, wherein determining the morphology dataset based on the optical dataset comprises:
determining a trace of a particle wall of the first particle captured in the optical dataset;
translating the trace into polar coordinates;
applying a discrete Fourier transform to the polar coordinates; and
determining a deformation metric for the first particle based on a harmonic of the discrete Fourier transform.

10. The method of claim 9, wherein determining the morphology dataset based on the optical dataset comprises:
determining a series of deformation metrics for the first particle as a function of particle x-position along the fluidic pathway, wherein the series of deformation metrics comprises the deformation metric; and
determining a series of aspect ratio values for the first particle as a function of the particle x-position along the fluidic pathway, wherein a first x-position corresponding to a local peak of the series of aspect ratio values is staggered from a second x-position corresponding to a local peak of the series of deformation metrics.

* * * * *

UNITED STATES PATENT AND TRADEMARK OFFICE
CERTIFICATE OF CORRECTION

PATENT NO. : 10,252,260 B2
APPLICATION NO. : 15/477973
DATED : April 9, 2019
INVENTOR(S) : Henry Tse, Katherine Crawford and Ajay Shah Page 1 of 1

It is certified that error appears in the above-identified patent and that said Letters Patent is hereby corrected as shown below:

In the Claims

Column 24, Line 67, after "comprises:", insert --¶--

Signed and Sealed this
Third Day of March, 2020

Andrei Iancu
*Director of the United States Patent and Trademark Office*